United States Patent
Ryadnov et al.

(10) Patent No.: US 10,265,403 B2
(45) Date of Patent: Apr. 23, 2019

(54) CYCLIC PEPTIDE

(71) Applicant: THE SECRETARY OF STATE FOR BUSINESSS, INNOVATION & SKILLS OF HER MAJESTY'S BRITANNIC GOVERNMENT, London (GB)

(72) Inventors: Maxim Ryadnov, Teddington (GB); Nilofar Faruqui, Teddington (GB); Angelo Bella, Teddington (GB); Jascindra Ravi, Teddington (GB); Santanu Ray, Teddington (GB); Baptiste Lamarre, Teddington (GB)

(73) Assignee: NPL MANAGEMENT LIMITED, Teddington, Middlesex (GB)

( * ) Notice: Subject to any disclaimer, the term of this patent is extended or adjusted under 35 U.S.C. 154(b) by 0 days.

(21) Appl. No.: 15/036,035

(22) PCT Filed: Nov. 13, 2014

(86) PCT No.: PCT/GB2014/053364
§ 371 (c)(1),
(2) Date: May 11, 2016

(87) PCT Pub. No.: WO2015/071666
PCT Pub. Date: May 21, 2015

(65) Prior Publication Data
US 2016/0279247 A1   Sep. 29, 2016

(30) Foreign Application Priority Data
Nov. 15, 2013  (GB) .................................. 1320209.8
Dec. 20, 2013  (GB) .................................. 1322749.1

(51) Int. Cl.
*C07K 7/64*   (2006.01)
*A61K 35/36*   (2015.01)
*A61K 47/42*   (2017.01)
*C07K 14/00*   (2006.01)

(52) U.S. Cl.
CPC .............. *A61K 47/42* (2013.01); *A61K 35/36* (2013.01); *C07K 7/64* (2013.01); *C07K 14/001* (2013.01)

(58) Field of Classification Search
None
See application file for complete search history.

(56) References Cited

PUBLICATIONS

Ryadnov et al. ("Modular Design of Peptide Fibrillar Nano-to Microstructures" J.Am.Chem.Soc. vol. 131(37) 2009).*
Angelo Della et al. "Arbitrary Self-Assembly of Peptide Extracellular Microscopic Matrices", Angewandte Chemie International Edition, vol. 51, No. 2, pp. 428-431 (2011).
Maxim G. Ryadnov et al. "Modular Design of Peptide Fibrillar Nano-to Microstructures", Journal of American Chemical Society Communications, vol. 131, pp. 13240-13241, (2009).

* cited by examiner

*Primary Examiner* — Jennifer Pitrak McDonald
*Assistant Examiner* — Tara L Martinez
(74) *Attorney, Agent, or Firm* — James S. Keddie; Bozicevic, Field & Francis LLP

(57) ABSTRACT

A cyclic peptide (10) includes two domains (D1,D2), each including three charged sub-domains (14, 16). The first domain (D1) includes two anionic sub-domains (14) followed by a cationic sub-domain (16). The second domain (D2) includes two cationic sub-domains (16) followed by an anionic sub-domain (14). The two domains are connected to one another and separated by a tri-glycyl linker (12). The cyclic peptide (10) is able to self-assemble into a network able to mimic an extracelluar matrix, and which promotes cell growth while resisting biofilm formation.

12 Claims, 15 Drawing Sheets
Specification includes a Sequence Listing.

I = HBTU/DIPEA in DMF
II = 20% piperidine in DMF
III = Pd(PPh$_3$)$_4$ in CHCl$_3$/AcOH/DIPEA
IV = TFA/TIS/H$_2$O (95:2.5:2.5)
Z = EIAALEGGGEIAALEQEIAALEYKIAALKGGGKIAALKQKIAALK Fig. 3a
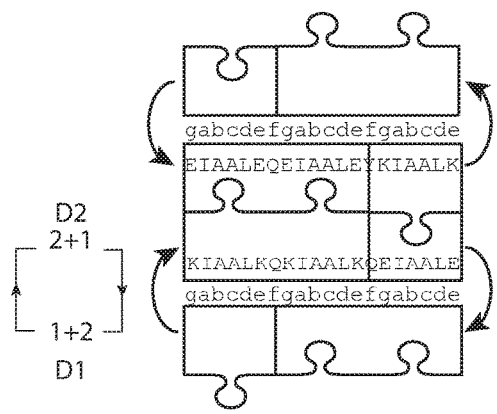
Fig. 3b
Fig. 3c
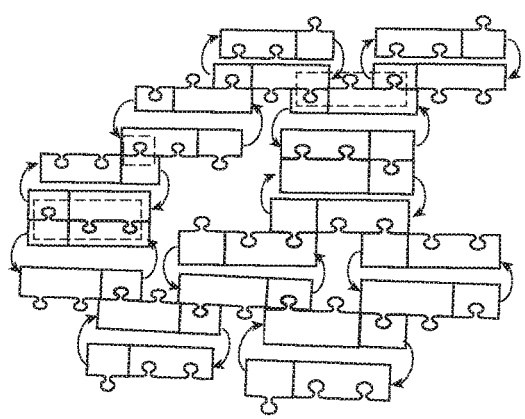
KIAALKQKIAALKQ
Fig. 3d
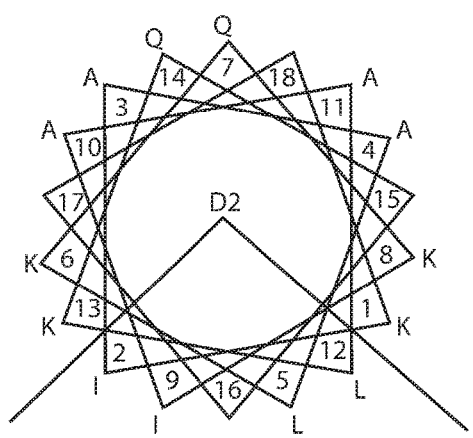

Size Distribution by Intensity

CYCLIC PEPTIDE

CROSS-REFERENCE

This application is a 35 U.S.C. 371 National Phase of International Application Serial No. PCT/GB2014/053364, filed Nov. 13, 2014, which application claims priority to GB 1320209.8 filed Nov. 15, 2013 and GB 1322749.1 filed Dec. 20, 2013, which are incorporated herein by reference in their entirety.

This invention relates to a cyclic peptide, and to a synthetic protein network formed therefrom. In particular it relates to a miniprotein able to form differentially instructive extracellular protein micro-nets and bioinspired, non-gelating protein micro-nets as differential extracellular matrices, which promote cell growth and prevent biofilm formation. The present invention also relates to methods of forming the nets using the cyclic peptide.

An ability to construct biological matter from the molecule up holds promise for applications ranging from nanobiotechnology to synthetic biology. Biomolecular self-assembly is nature's strategy of biomaterial construction, which can be programmed to support desired function. A challenge remains in replicating the strategy synthetically, that is at will, and differentially, that is for a specific function at a native length scale.

Synthetic extracellular matrices are useful for a variety of applications, and increasingly so for modern molecular medicine for which novel materials that direct biology the way nature does are in steady demand. Peptide self-assembly offers a particularly attractive strategy as it can mimic native designs from the bottom up. Existing mimetics are anisotropic fibrillar structures characterised by unidirectional near-crystalline order, which though provides control over fibrillogenesis, may limit topographical cues to nanometer scales. By contrast, native extracellular matrices allow significant orthogonality in their assembly thereby generating multi-scale fibrillar networks and meshes. Although it is possible to render synthetic assemblies orthogonal with the help of co-assembling specialist blocks, resulting morphologies span similar nanometer dimensions within which functional cell support may not be efficient. Indeed, rigidified nanoscale geometries cannot readily accommodate subtle morphological alterations that are inevitable in dynamic cellular environments. They may confine such changes to sub-microscopic niches, which is sufficient for supporting local adhesive contacts promoting integrin-mediated attachments, but cannot support contiguous cellular recruitment across larger length scales.

Structurally adaptive strategies are devised to provide more efficient solutions and can be exemplified by biocatalytic induction and pairwise axial interactions to access higher ordered structures with a better control over assembly and stability or primary amphiphile displays having high densities of binding epitopes. Such designs are typically supported by gelation, with their architectures, in contrast to the native matrices, not necessarily being characteristic of structurally persistent and regular networks having mesh sizes exceeding several microns. DNA tile self-assembly which may help tackle the problem of mimicking protein fibrillogenesis, is not restricted to nanometer length scales and can afford persistence lengths that can be tuned to support cell adhesion.

However, the question remains as to the ability to structurally program a non-gelated protein mimetic of native matrices. This is the microscale architecture of protein matrices that ensures different biological functions ranging from cell adhesion to mucosal innate immunity, which are often expressed in combination. Therefore, the main emphasis should be on those synthetic mimetics that enable matrix architectures able to elicit differential biological responses at the microscopic length scales—a synthetic ability that has yet to emerge.

In summary, known self-assembling peptide-protein-based products that support cell growth suffer from one or more of the following drawbacks:

They span only nanometer to micrometer dimensions and have low and small porosity They are of individual protein fibrils that are not physically connected into continuous (uninterrupted) networks and meshes They are largely based on beta-structure assembly, which can lead to amyloidogenesis They are toxic to cells and tissues They are not antimicrobial They are in the form of a gel, which is subject to erosion.

According to an aspect of the present invention, there is provided a cyclic peptide including a first domain and a second domain, the first domain and the second domain connected to one another at each end by a linker, wherein each domain includes a plurality of charged sub-domains and includes at least one cationic sub-domain and at least one anionic sub-domain.

The cyclic peptide, which may also be termed a miniprotein, is able to self-assemble into microscopic fibrillar nets.

In an embodiment, within each of the first domain and the second domain there is not an equal number of cationic sub-domains and anionic sub-domains.

The first domain and the second domain may each include at least three sub-domains. Preferably the first domain and the second domain include an odd number of sub-domains, for example, three sub-domains.

In an embodiment, the first domain and the second domain do not have the same number of cationic sub-domains as one another, and wherein the first domain and the second domain do not have the same number of anionic sub-domains as one another.

Preferably, the first domain has more anionic sub-domains than cationic sub-domains, and the second domain has more cationic sub-domains than anionic sub-domains.

In an embodiment, the anionic sub-domains are located at the amino-end of the first domain and at the carboxyl-end of the second domain, and wherein the cationic sub-domains are located at the carboxyl-end of the first domain and the amino-end of the second domain. Alternatively, the anionic sub-domains may be at the carboxyl-end of the first domain and the amino-end of the second domain, and the cationic sub-domains may be at the amino-end of the first domain and the carboxyl-end of the second domain.

In a preferred embodiment the first domain has two anionic sub-domains and one cationic sub-domain, and the second domain has two cationic sub-domains and one anionic sub-domain.

At least one of the sub-domains may have seven amino acids and/or at least one of the sub-domains may have six amino acids. Each domain may comprise two sub-domains having seven amino acids and a sub-domain having six amino acids. Optionally, the sub-domain having six amino acids may be located at the carboxyl-end of the domain.

A sub-domain may include a sequence of polar (P) and hydrophobic (H) amino acids as follows: PHPPHP, optionally followed by a further polar amino acid. For example, an anionic sub-domain may include the following amino acid sequence: EIAALE (SEQ ID NO: 1), optionally followed by Q or Y, and/or a cationic sub-domain may include the following amino acid sequence: KIAALK (SEQ ID NO: 2), optionally followed by Q. In a preferred embodiment, the first domain has the sequence: EIAALEQEIAALEYKI-AALK (SEQ ID NO: 3) and/or the second domain has the sequence: KIAALKQKIAALKQEIAALE (SEQ ID NO: 4).

In an embodiment, the cyclic peptide may have the formula:

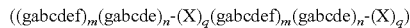

where gabcdef is a heptad repeat motif, X is a flexible linker; m≥2; n≥1; and q=1.

The linker may include three amino acids. The linker may include a plurality of glycine residues. The cyclic peptide may include at least one tri-glycyl linker. In a preferred embodiment, the cyclic peptide includes two tri-glycyl linkers.

In a preferred embodiment, the cyclic peptide has the sequence:
(EIAALEQEIAALEYKIAALKGGGKIAALKQKI-AALKQEIAALEGGG) (SEQ ID NO: 5)

According to another aspect of the present invention, there is provided a synthetic protein network formed from a cyclic peptide as defined above.

The network may be a synthetic extracellular matrix.

The synthetic protein network may include eukaryotic cells, for example vertebrate cells, grown thereon.

According to another aspect of the present invention, there is provided a method of making a synthetic protein network, including providing a cyclic peptide as defined above, and allowing the cyclic peptide to self-assemble into the synthetic protein network.

Preferred embodiments of the invention provide protein biomaterials spanning sub-millimeter dimensions that can support and instruct the initial stages of cell growth and development under bacteria-challenged conditions. Mammalian cell attachment is enhanced, whilst bacterial adsorption, colonisation and biofilm formation are prevented.

The applicant has developed a structural rationale for the programming of sub-millimeter matrix architectures, which support adhesion, growth and proliferation of mammalian cells and which efficiently resist biofilm formation. The design is preferably a single peptide block providing a self-assembly topology, which is (i) free of directionality constraints, (ii) spans microscopic dimensions and (iii) is biologically differential. The self-assembly topology enables a net-like architectural mimetic of the extracellular matrix capable of eliciting differential biological responses—mammalian cell growth and proliferation, and biofilm resistance—at the native sub-millimeter length scales. The biological performance of these synthetic nets directly correlates with their morphological and chemical properties promoting thus an application model for differential extracellular matrices.

Preferred embodiments of the present invention are now described, with reference to the accompanying drawings, in which:

FIG. 3 illustrates the design of a preferred cyclic peptide (FIG. 3A: SEQ ID NO: 3; FIG. 3C: SEQ ID NO: 11);

ABBREVIATIONS

All—allyl; DIPEA—diisopropylethylamine; Fmoc—9-fluorenylmethoxycarbonyl; FTIR—Fourier transform infrared spectroscopy; HBTU—O-benzotriazole N,N,N',N'-tetramethyluronium-hexafluorophosphate; MALDI-ToF—matrix-assisted laser desorption/ionisation time of flight; MOPS—3-(N-morpholino)propanesulfonic acid; QCM-D—quartz crystal microbalance with dissipation; RP-HPLC—reversed phase high pressure liquid chromatography; TIS—triisopropylsilane; TFA—trifluoroacetic acid; XRD—x-ray diffraction.

Figure 1:
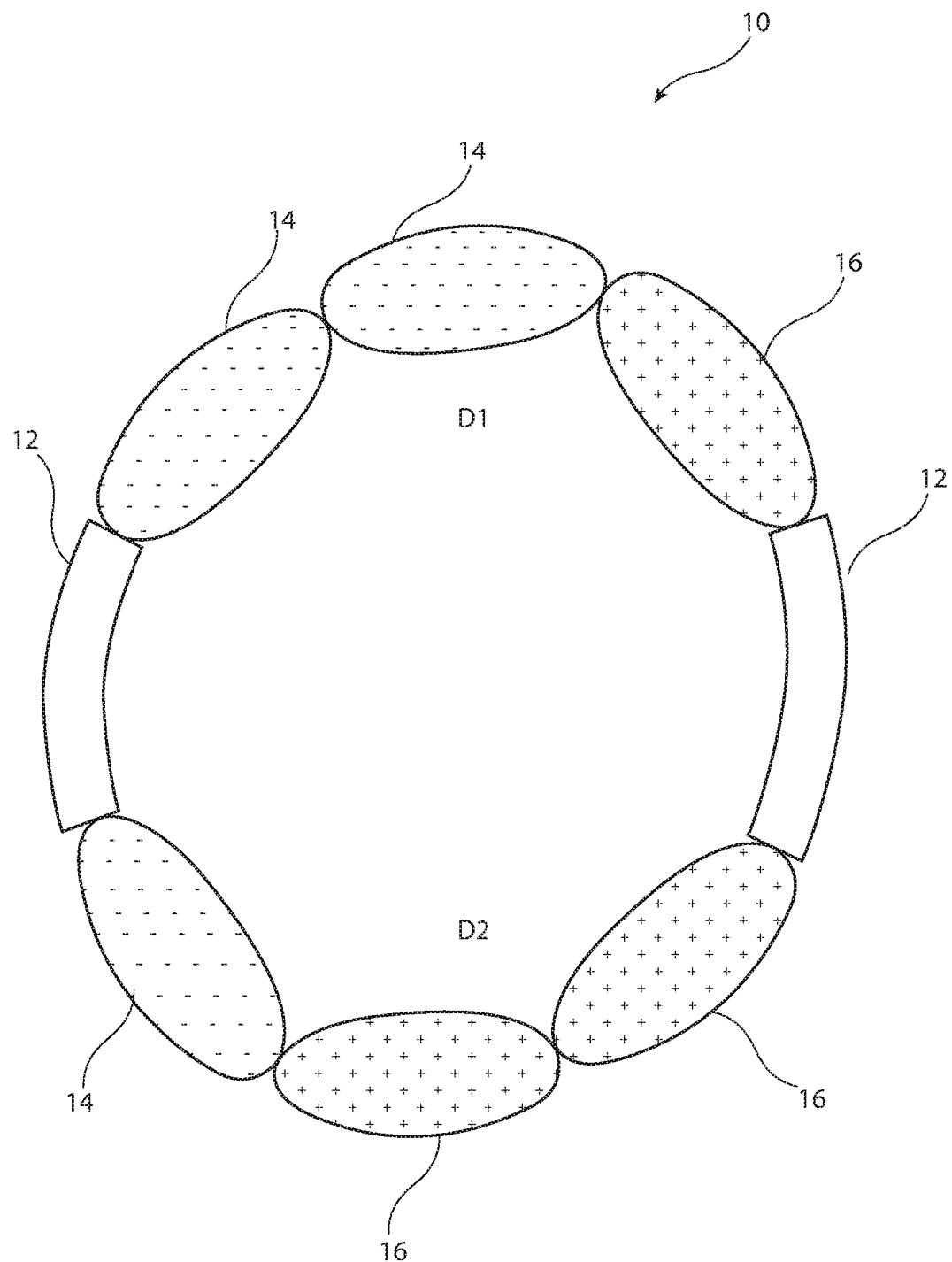
FIG. 1 is a schematic representation of a cyclic peptide in accordance with an embodiment of the invention.

FIG. 1 schematically illustrates a cyclic peptide 10 in accordance with a preferred embodiment of the invention. The cyclic peptide 10 includes a first domain D1 and a second domain D2, connected to one another by linkers 12. The linkers 12 may be formed from any suitable amino acid. Preferably, however, the linkers include glycine residues as these are small and functionally inert. Tri-glycyl linkers may be suitable, for example.

Figure 2:
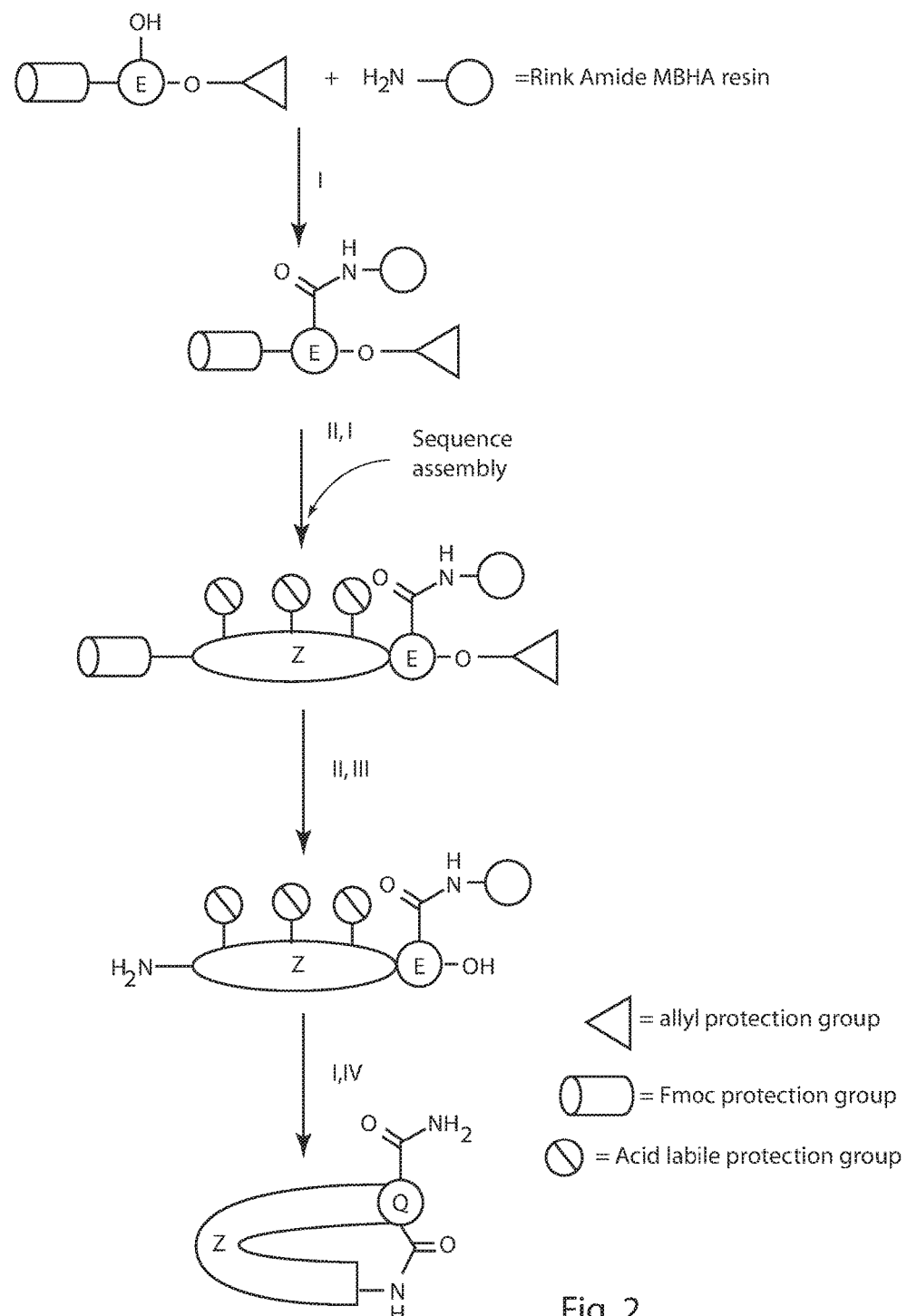
FIG. 2 is a schematic representation of the synthesis of a cyclic peptide in accordance with an embodiment of the invention (SEQ ID NO:10)

In a preferred embodiment, the topology is a cyclised sequence of α-helical heptad repeats of polar (P) and hydrophobic (H) residues. In a particular embodiment, each heptad subdomain 14,16 has the pattern: PHPPHP(P), which is derived from archetypal coiled-coil motifs. Two complementary repeats (anionic 14 and cationic 16 respectively) arrange into an asymmetric pattern to make up the two domains D1,D2 each comprising three sub-domains 14,16. Domain D1, contains, in order (in the amino- to carboxyl-direction), two anionic sub-domains and one cationic sub-domain, whereas domain D2 has the reverse arrangement. In a particularly preferred embodiment, the anionic sub-domain 14 has the sequence EIAALEQ/Y and the cationic sub-domain 16 has the sequence KIAALKQ, with the sub-domain at the carboxyl-end including only the first six of the amino acids in each case (FIGS. 1, 2 and Table 1).

TABLE 1

Peptide constructs used in the study

| Name | Sequence |
|---|---|
| | gabcdefgabcdefgabcde  gabcdefgabcdefgabcde |
| SaNet | (EIAALEQEIAALEYKIAALK-GGG-<br>KIAALKQKIAALKQEIAALE-GGG)[a] (SEQ ID NO: 5) |

TABLE 1-continued

Peptide constructs used in the study

| Name | Sequence gabcdefgabcdefgabcde gabcdefgabcdefgabcde |
|---|---|
| D1 | EIAALEQEIAALEYKIAALK-am (SEQ ID NO: 3) |
| D2 | KIAALKQKIAALKYEIAALE-am (SEQ ID NO: 9) |

The product may be provided as a lyophilised protein in the form of a powder that is easily prepared, transported and reconstituted in aqueous biocompatible media. Lyophilisation can be carried out using standard freeze-drying techniques. For example, the peptide is dissolved in water and then frozen at −20° C. or using liquid nitrogen, and then dried under a vacuum to obtain an amorphous white material. Upon reconstitution in an aqueous buffer, the peptide spontaneously self-assembles into a matrix or network, which is referred to as SaNet (self-assembling net), and which is described in more detail below.

FIG. 3a is a schematic representation of the SaNet topology with a 2+1 asymmetric pattern of the sub-domains 14,16 in the two domains D1,D2. One puzzle piece denotes one sub-domain. Heptad repeats designated gabcdef (see Table 1) are shown above the linear sequences highlighted in the blocks. The arrows indicate the N-to-C directionality of the sequences. Each arrow is a triglycyl linker.

FIG. 3b illustrates the domain sequences configured onto coiled-coil helical wheels with 3.5 residues per turn. Curved double-headed arrows indicate electrostatic interactions between g and e (circled); crossed arrows show a hydrophobic interface of a heterodimer favoured by isoleucines and leucines in a and d respectively; b, c and f are solvent-exposed and are small and neutral alanines and glutamines; a single f site is made tyrosine to allow concentration measurements using absorbance at 280 nm.

The split 2+1/1+2 pattern enables arbitrary interactions between the domains D1,D2 promoting various heptad overlaps. This is illustrated in FIG. 3c, which is a simplified representation of the SaNet assembly with one-, two- and three-heptad overlaps highlighted by dashed lines.

FIG. 3d illustrates the cationic stretch of the second domain D2 sequence configured onto an antimicrobial helical wheel with 3.6 residues per turn showing the clustering of amino acid residues into two distinctive polar and hydrophobic faces.

Cyclisation renders the topology orthogonally closed making each of the overlaps probable in any direction with respect to the plane of the cycle. The orientation of the domains D1,D2 in the cyclopeptide is antiparallel which ensures interactions between different peptides and not within the same peptide. This is reinforced by the two triglycyl linkers that fix the domains D1,D2 at their termini favouring outward interactions (see FIGS. 1 and 3a). The resulting bifaceted block assembles through heptad overlaps or "knots" (FIGS. 3a and 3c). Three-heptad knots maintain continuous lateral assembly, which ensures fibre formation, while less stable one-heptad overlaps propagate longitudinally through cooperative two-heptad knots (FIG. 3c). The overall assembly is thus indiscriminate and can re-direct at any point. This is expected to yield mesoscopic net-like structures of fibres with broad width distributions. We refer to this topology as a Self-assembling Net (SaNet).

The applicant has developed a single-peptide self-assembly topology, which adopts a helical type of folding, stable and reversible, and which enables the assembly of fibrous matrices, microscopic and biologically differential. The described SaNet is a synthetic approximation of the native extracellular matrices, which shares key physico-chemical characteristics of the native systems including nanoscale order, hyper branched and knotted morphology and high persistence length of fibrillar structures. All these properties contribute to the formation of intricate fibrous networks that span nano-to-sub-millimeter dimensions thereby allowing for the continuous expression of unique bio-functional characteristics programmed in the sequence, i.e. antimicrobial carpets and filopodia-recognised adhesion points. SaNet is the first synthetic topology that generates microscopic knotted matrices whose biological performance, scaffold support for mammalian cell proliferation and resistance against biofilm formation, correlates with their morphological and chemical properties promoting thus an architectural model for differential extracellular matrices.

The cyclic peptide can be modified to incorporate specific cell adhesion motifs and/or factors, or cleavage sites for matrix proteinases that might facilitate matrix remodelling. Adhesion motifs may be covalently attached to a complementary domain (anionic or cationic) derived from D1 or D2, which is added to a pre-assembled matrix to decorate its surface. Alternatively, adhesion and cleavage sites can be incorporated into the sequence of the cyclic peptide at the linker sites.

The synthetic network formed from the cyclic peptide could be used in many fields of technology. For example, it could be used in wound healing, tissue engineering, biomaterials, single-cell film production, cell-matrix studies, contact lens coatings, skin and cloth patches (for example, to detect microorganisms in the environment), antimicrobial skin patches (for example for blisters to prevent infection), surgical tape, adhesive skin closures. By way of example, the matrix could be pre-assembled and introduced into a wound site as a coating, or the peptide could be introduced into a wound site and assembled in situ. It could also be used to coat a solid substrate for cell culture to allow for cell proliferation, differentiation an growth of new tissue in vitro.

Preferred embodiments of the technology combine several properties into one living biomaterial, which provides:
Sub-millimeter networks assembled from one small protein
Biofilm resistance
Bio-functional substrate for cell growth and proliferation
Physico-chemical cues enhancing cellular responses via substantially increase numbers of filopodia
Thin (micrometer scale) film surface coating.

EXAMPLES

Example 1—Peptide Design and Synthesis

All peptides (see Table 1) were assembled on a Liberty-1 microwave peptide synthesiser (CEM Inc.) using solid phase Fmoc/tBu protocols and HBTU/DIPEA as coupling reagents.

The synthesis steps are schematically illustrated in FIG. 2. Allyl-based orthogonal protocols were used for cyclisation on resin. Rink amide 4-methylbenzhydrylamine resin was used throughout. Fmoc-Glu(OH)-OAII was used as a C-terminal residue attached via its γ-carboxyl to assemble and cyclise the SaNet peptide. Upon cleavage and deprotection (95% TFA, 2.5% TIS, 2.5% water) this Glu was converted into Gln. The identities of the peptides were confirmed by analytical RP-HPLC and MALDI-ToF.

Analytical and semi-preparative gradient RP-HPLC was performed on a JASCO HPLC system using Vydac C18 analytical (5 mm) and semi-preparative (5 mm) columns. Both analytical and semi-preparative runs used a 10-60% B gradient over 50 min at 1 mL/min and 4.7 mL/min respectively with detection at 230 and 220 nm. Buffer A—5% and buffer B—95% aqueous $CH_3CN$, 0.1% TFA.

MS [M+H]+: SaNet—m/z 4644.5 (calc), 4645.8 (observed); D1—m/z 2186.6 (calc.), 2187.3 (observed); D2—m/z 2184.7 (calc.), 2186.1 (observed). [M+Na]+ were also observed.

Example 2—Assembly and Folding

To allow self-assembly into a matrix, 200 µL samples (100 µM in each peptide or as stated otherwise) were incubated overnight in 10 mM MOPS or phosphate buffer, pH 7.4, 20° C., after which 50 µL of peptide solutions were mounted onto an appropriate substrate (see corresponding sections below for microscopy, cell assays, biofilm formation, and impedance measurements) and buffer excess was removed by blotting paper. Similarly, 50 µL of protein solutions (500 µg/mL) were used to prepare fibronectin- and collagen-coated substrates.

High resolution confocal images were acquired using a confocal laser scanning microscope (LEXT OLS3100) equipped with 408 nm LD class 2 laser with 5-100× objective lenses giving a total magnification of 120-14400×. Images were processed using the proprietary software. Optical micrographs were acquired on an Olympus CX40 microscope connected with high resolution CCD camera using a magnification of 50× objective MPLN Plan Achromat lenses. No image processing was performed after image acquisition.

For atomic force microscopy (AFM) imaging, a drop (5-10 µL) of the pre-incubated 100-µM solution of peptide in 10 mM MOPS (pH 7.4) was deposited on a clean silicon wafer and the buffer excess was removed by blotting paper. AFM images were obtained using an MFP-3D system (Asylum Research Ltd.). All measurements were carried out in tapping mode using PPP-NCHR type cantilevers (Nanosensors™). The cantilevers were coated with 30-nm thick aluminium on the detector side to enhance the reflectivity of the laser beam. A typical value of the cantilever resonance frequency was about 330 kHz and force constant 42 N/m. Images were processed using proprietary SPIP software, version 6.0.13. To minimise variations in the spatial resolution resulting from wear of the tip, the cantilevers were changed regularly.

Figure 4A:
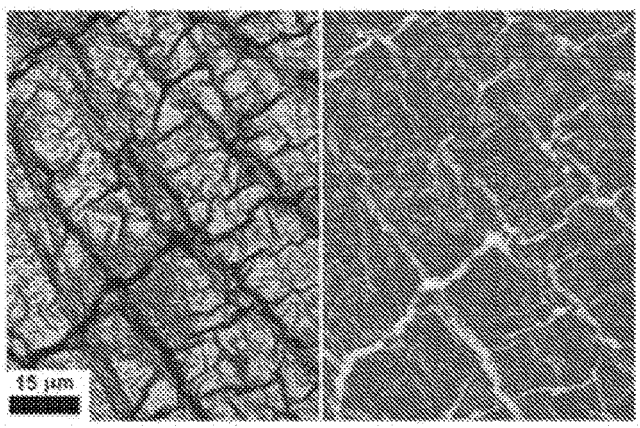
FIGS. 4 and 5 show the results of studies on assembled networks formed from an embodiment of a cyclic peptide.
Figure 4B:
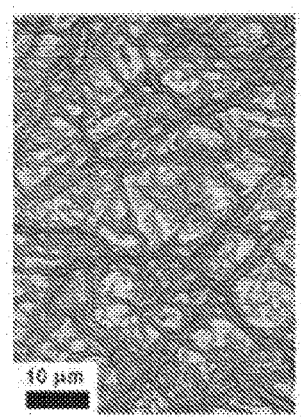
Figure 4C:
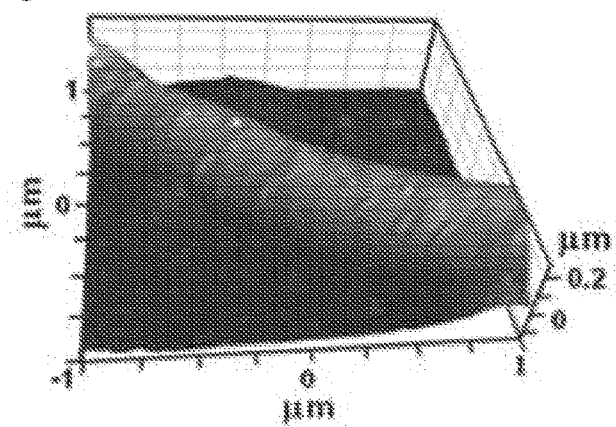
Figure 4D:
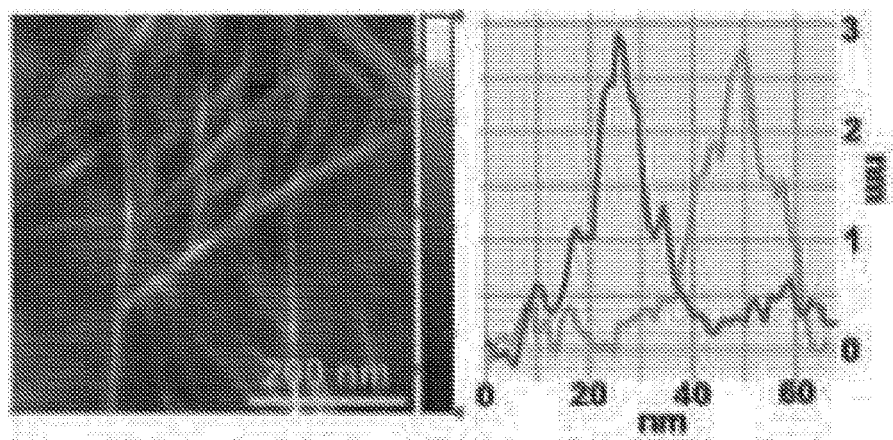
Figure 5A:
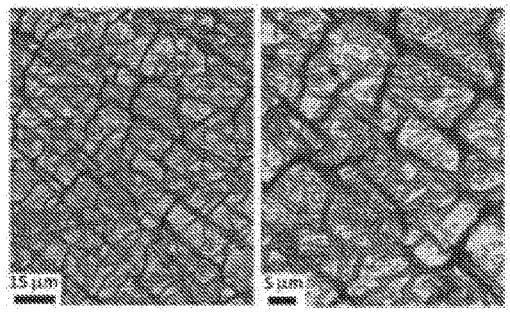
Figure 5B:
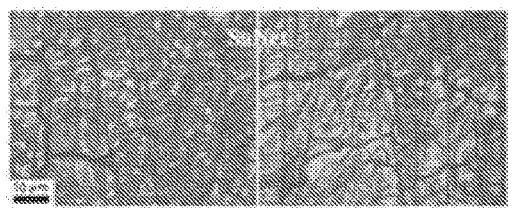
Figure 5C:
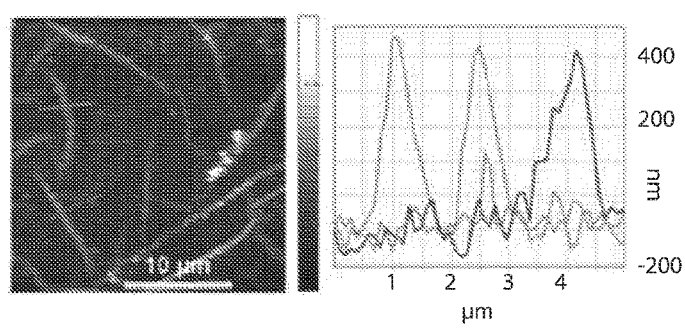
Figure 5D:
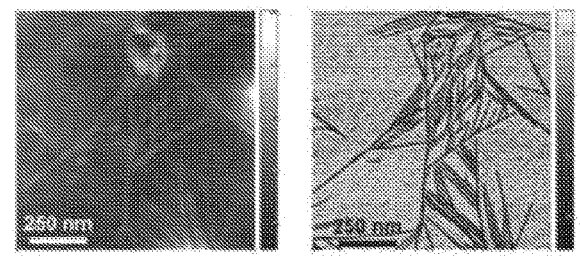
Figure 5E:
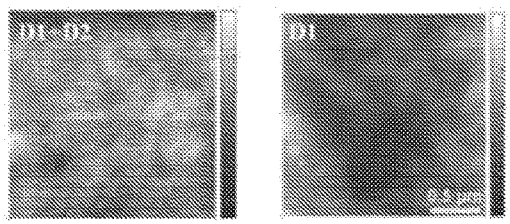
Figure 5F:
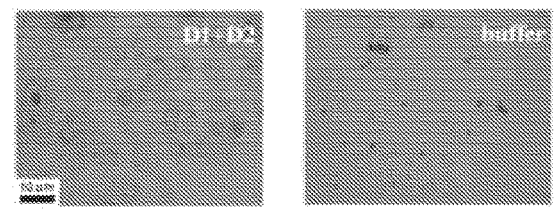

Confocal, optical and atomic force microscopy revealed irregular and densely knotted nets formed by relatively short intersecting fibre networks (see FIGS. 4, 5a and 5b). FIGS. 4a and 4b are confocal and optical micrographs respectively of higher order networks. The colour-inverted image (FIG. 4a) highlights clusters of lower order assemblies (the darkest areas). FIG. 4c is an AFM topography image of a high order fibre, and FIG. 4d is an AFM topography image of lower order fibrillar branches with cross sections along the highlight lines. FIGS. 5a and 5b are confocal and optical micrographs respectively of SaNet. FIGS. 5c and 5d are AFM images of higher order fibres with cross sections along the highlight lines (c) and lower fibrillar branches (d, topography image, left, and phase image, right). FIGS. 5e and 5f are AFM and optical micrographs respectively of controls (see below).

The structures extended tens of microns in length with fibre thicknesses ranging from 200 nm to ~1 µm, which was in good agreement with size distributions obtained by dynamic light scattering measurements (FIGS. 4a-c, FIG. 5c and FIG. 6a). Dynamic light scattering batch measurements were carried out by photon correlation spectroscopy on a Zetasizer Nano (ZEN3600; Malvern Instruments, Worcestershire, UK), in a low volume (100 µL) disposable cuvette at 25° C. No filtration of peptide samples was carried out before the measurements so that assembly populations remain unaffected. Hydrodynamic radii were obtained through the fitting of autocorrelation data to a single exponential function using the manufacture's software, Dispersion Technology Software (DTS version 5.10).

Figure 6A:
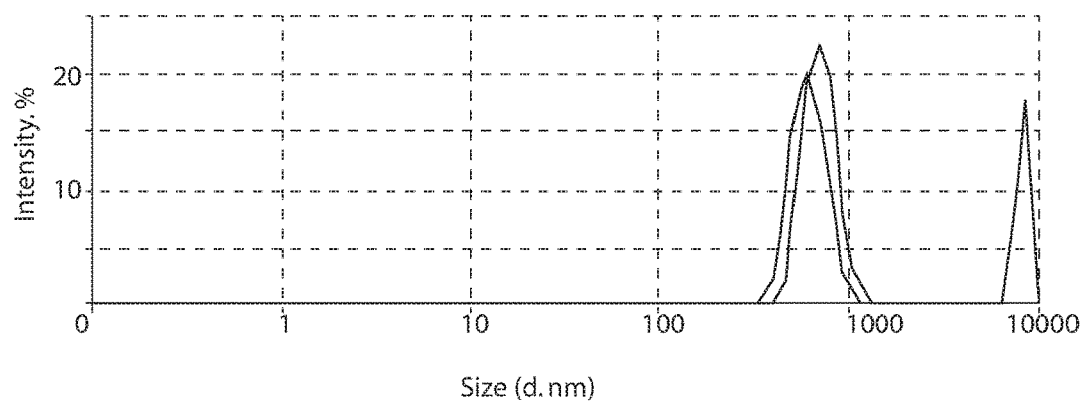
FIG. 6 shows dynamic light scattering traces and QCM-D responses.

FIG. 6a shows dynamic light-scattering traces for SaNet of three independent measurements. The values in the Table correspond to the trace shown as a dotted line. Developing or lower order networks, which were dominated by periodic branching and patching of growing branches (FIGS. 4d and 5d), were also observed. AFM analyses of these lower order branches gave conservative thicknesses of ~3 nm suggesting a lateral packing of the folded peptide blocks along the fibre axis (FIG. 4d).

The SaNet block is of a 2×3 nm rod-shaped mesogen, in which the cyclic backbone, which rigidifies upon folding, is likely to provide a near-crystalline order through cooperative three-heptad knot interactions, when complementary helices are fully aligned with all electrostatic interactions satisfied, and staggered knot interactions, when only some inter-helical interactions are satisfied, which provide a network-like propagation (FIG. 3c). 10 nm widths of the small fibres may account for the side-by-side assembly of 2 nm thick protofilaments, which upon organising into higher order assemblies entangle through branching patches with the formation of arbitrary net points. The persistence length of higher order fibres was high, so was the rate and frequency with which branching was generated. Therefore, the assembly might undergo two independent but synergistic processes including persistent nucleation of branching and a homeotropic stack-like alignment of the cyclopeptide blocks in a fashion similar to that of amyloid assemblies. Additionally, in some cases fibre networks tended to associate with clusters of pool-like assemblies that were also rich in low order branching (FIG. 4a).

Consistent with these observations, control mixtures of individual D1 and D2 (D1+D2) (see Table 1), which in principle can form three-heptad interactions and build upon each other, did not propagate (FIGS. 5e and 5f). To assemble, these blocks have to be in register, which, in contrast to the SaNet, is compromised by competitive interactions between the same domains (FIG. 3). The stacking of SaNet blocks largely propagates through three-heptad interactions, which, unlike amyloid in cross-β spines, is interrupted by one- and two-heptad interactions imposing directionally promiscuous assembly (FIG. 3c).

Figure 7A:
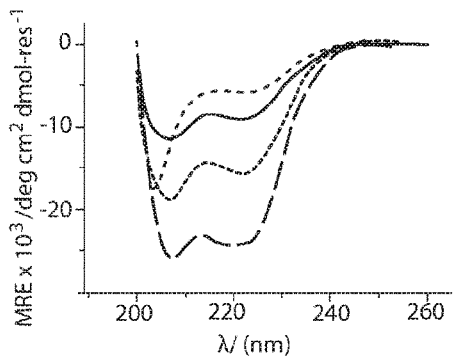
FIG. 7 shows the results of studies on the folding of an embodiment of a cyclic peptide.
Figure 7B:
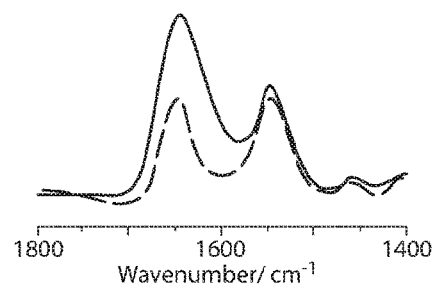
Figure 7C:
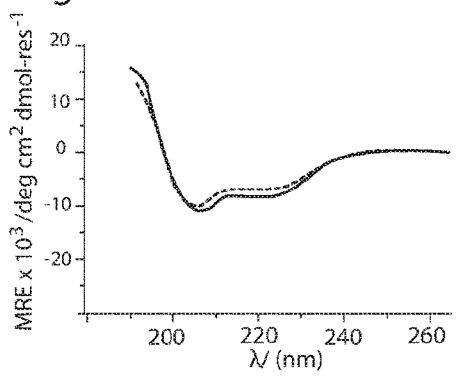

Such synergy in the SaNet assembly proved to be compatible with designed helical folding as confirmed by circular dichroism (CD) and Fourier transform infrared (FTIR) spectroscopies as shown in FIGS. 7a and 7b.

CD spectra were recorded on an Applied Photosystem Chirascan spectropolarimetre fitted with a Peltier temperature controller. All measurements were taken in ellipticities in mdeg and after baseline correction were converted to mean residue ellipticity (MRE; deg $cm^2$ dmol $res^{-1}$) by normalising for the concentration of peptide bonds and cuvette pathlength. Aqueous peptide solutions (300 µL, 100 µM in each peptide unless stated otherwise) were prepared in filtered (0.22 µm) 10 mM MOPS or phosphate buffer, pH 7.4. To calculate the percent α-helix, the equation, $-100([q]_{222}+3000)/33\,000)$, was used. FIG. 7a shows CD spectra for SaNet (solid line), D1-D2 (dashed line), D1 (dotted line) and D2 (space-dotted line).

All FTIR spectra were collected using a Tensor-37 series FTIR spectrophotometre with a BioATR II unit (Bruker Optics, UK) as the sampling platform with a photovoltaic mercury-cadmium telluride (MCT) detector and a Bruker Optics workstation equipped with OPUS software. Low volume (20 μL) peptide samples (100 mM, 10 mM MOPS, pH 7.4) were placed in a circular sampling area of radius 2 mm with path length of 6 μm. This multi-reflection ATR accessory is based on a dual-crystal technology, which has an upper silicon crystal and a hemispherical zinc selenide (ZnSe) lower crystal that does not come into contact with the sample. The temperature of the samples was maintained at 20° C. using a Peltier apparatus. All FTIR spectra were collected with resolution of 4 cm-1, scanner velocity of 20 kHz, 256 scans, phase resolution of 32, and zero filling factor of 4. FIG. 7b shows FTIR spectra for SaNet before (solid line) and after (dashed line) thermal denaturation. The helix content in the assembly was <25% and was lower than that for D1+D2 (35%) (FIG. 7a).

The partial loss of helicity may be due to the triglycyl linkers contributing elements of disorder. However, the thermal unfolding of the assembly revealed nearly complete reversibility of folding characteristic of a cooperatively folded structure, as shown in FIG. 3c, which shows CD spectra for SaNet before (solid line) and after (dashed line) thermal denaturation.

Thermal unfolding was probed by CD spectroscopy and the results are shown in FIG. 8. Thermal denaturation curves (solid lines) and their first derivatives (dashed lines) for SaNet (FIG. 8a), D1-D2 (FIG. 8b) and D1 (FIG. 8c); and CD spectra following the thermal unfolding of D1-D2 (FIG. 8d) and D1 (FIG. 8e); 10° C. (dotted line) and 90° C. (dashed line) with intervening spectra recorded every 10° C. (solid lines).

Figure 7D:
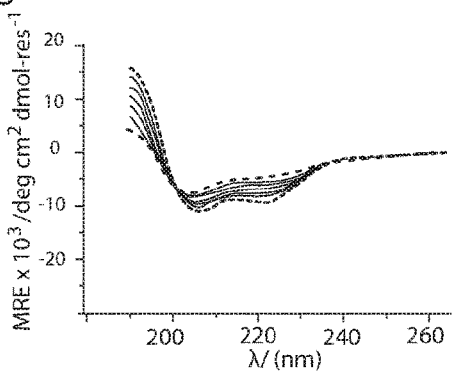
Figure 8A:
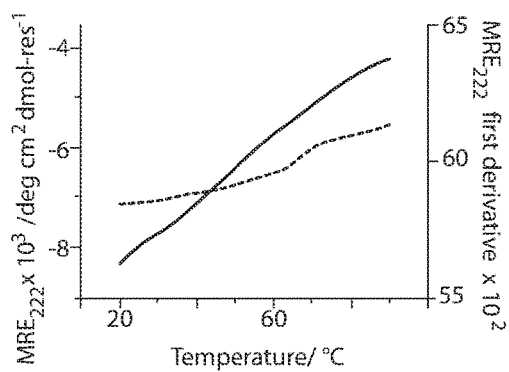
FIG. 8 shows thermal denaturation curves obtained by CD spectroscopy.
Figure 8B:
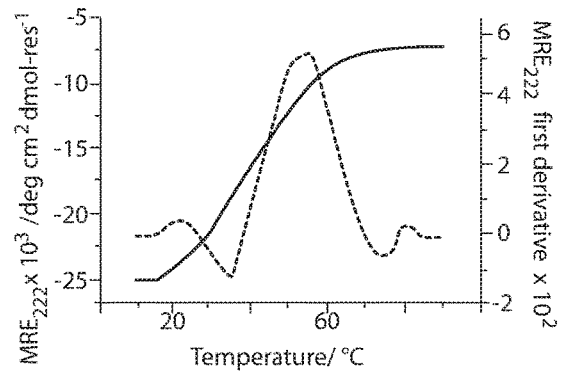

Thermal denaturation curves were approximately linear which is consistent with multiple helical assemblies and their partial fraying by the linkers (see FIG. 8a). Additional support for this came from a clear isodichroic point at 202 nm indicating a two-state transition between helical and unfolded forms (FIG. 7d, which shows CD spectra following the thermal unfolding of SaNet; 10° C. (dotted line) and 90° C. (dashed line) with intervening spectra recorded every 10° C. (solid lines) (note the isodichroic point at ~202 nm)), and from that the mixtures of individual and non-constrained domains D1+D2 gave perfectly sigmoidal curves, with their first derivatives dominated by a single transition midpoint of ~55° C. (FIG. 8b). Interestingly, although D2 did not fold, CD spectra for D1 were partially helical (FIG. 7a).

Figure 8C:
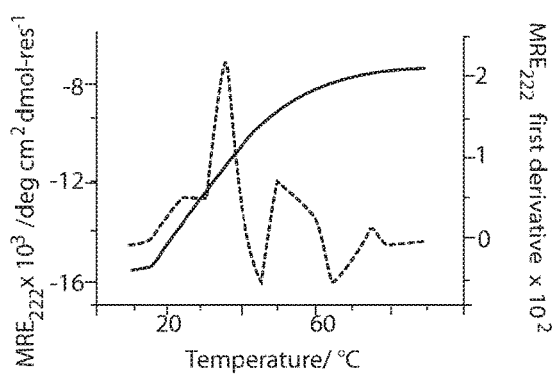
Figure 8D:
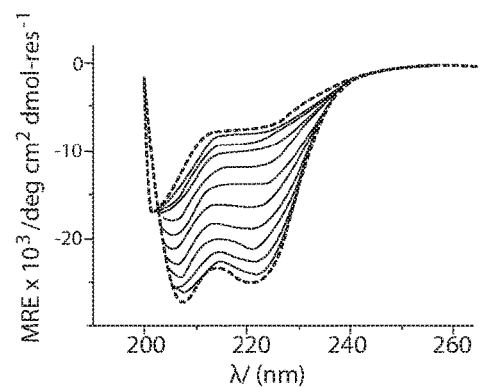
Figure 8E:
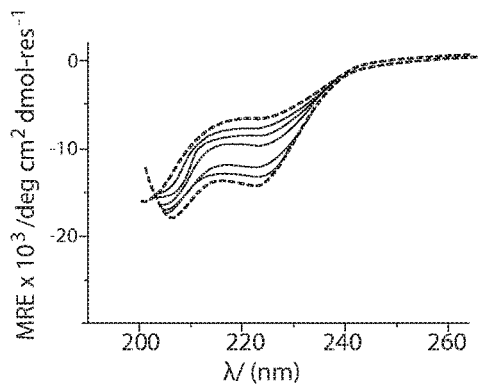

However, the first derivatives of the thermal denaturation curves for D1 revealed overlapping transitions of non-specific and possibly competing complexes (FIG. 8c). Furthermore, isodichroic points at 202 nm for both D1+D2 and D1 were less apparent suggesting equilibrium fluctuations between conformer populations (FIGS. 8d and 8e). As a result, D1 did not assemble (FIG. 5e).

Further evidence for the folding-mediated SaNet assembly was provided by X-ray diffraction (XRD) experiments using characteristic x-rays of λ=2.2897 Å This wavelength can obtain diffraction information from a depth of around 8 microns, which is compatible with the size and morphology of the assembled nets and with the sample preparation used for microscopy studies.

The XRD data were collected using Cr-Kα radiation (λ value of 2.2897 Å) on a Bruker D8 Discover diffractometre, with a D8 goniometre being set up in the Bragg-Brentano geometry using a θ-2θ drive. The incident X-ray beam was collimated using 1° slits. The diffracted beam was collected using a scintillation detector. The specimen wafers were held in place by a vacuum chuck and a 2θ scan was performed on each sample in turn from 5° to 80°. A step size of 0.02° 2θ was used with a count time per step of 0.4 seconds. After collection the background signal from the data was subtracted using the Bruker EVA programme prior to converting the file into a Microsoft Excel format. All measurements were performed at room temperature with tube settings of 30 mA 40 kV for all substrates prepared as for the AFM measurements.

Figure 7E:
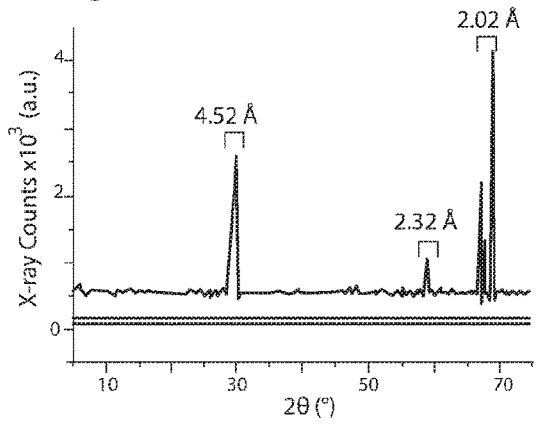

XRD patterns for the nets revealed a dominating d-spacing of ~4.52 Å (angle 2q of) 29-30° corresponding perfectly to an average radius of lowest-energy coiled-coil dimers and was accompanied by a minor d-spacing of ~2.32 Å (angle 2q of 59.5°) consistent with the radius of an ideal α-helix. Interestingly, average d-spacings of 2.02 Å derived from 68-69° peaks (2q), which appear to be in good agreement with a radius typical of $3_{10}$ helices (1.9 Å), were also observed (see FIG. 7e, which shows XRD patterns for SaNet (top trace), D2 (bottom trace) and D1+D2 (middle trace). These patterns suggest that long-range coiled-coil interactions provided by α-helical heptad overlaps may be accompanied by short and irregular para-helical regions ($3_{10}$). In marked contrast, no periodicities were detected for D2 and D1+D2 (FIG. 7e). The results in combination with the spectroscopy and microscopy data confirm near-crystalline periodicity for SaNet at the observed length scales.

With the nets assembled in solution showing no signs of cloudiness, gelation or turbidity at any stage of the assembly at the concentrations used, it was reasonable to probe SaNet elongation kinetics at a solution-surface interface. With this in mind, quartz crystal microbalance with dissipation (QCM-D) monitoring in real time was performed.

Continuous-flow QCM-D was performed as follows: QCM sensograms were recorded at 20° C. on a Q-Sense E1 instrument with a temperature-controlled fluid cell (Q-sense, Sweden). Peptide solutions (100 μM in 10 mM MOPS, pH 7.4) were passed over silicon dioxide coated quartz crystals (10 mm in diameter), with a fundamental frequency of about 5 MHz crystals, to continuously monitor adsorption. Following an equilibration phase (zone I in FIG. S2b) peptide solutions were run at a continuous flow rate of 5 μL/min (Zone II, FIG. S2b). Obtained data was analysed using the proprietary Q-Tools software. The measurements were performed at several harmonics (n=3, 5, 7, 9, 11 and 13). Δf and ΔD were fitted for the third overtone using the Q-Tools software. The first resonance is generally perturbed by edge effects caused by the crystal mount. The results are presented as changes in resonance frequency (Δf) and dissipation (ΔD) with time due to peptide adsorption on the crystal surfaces.

Figure 7F:
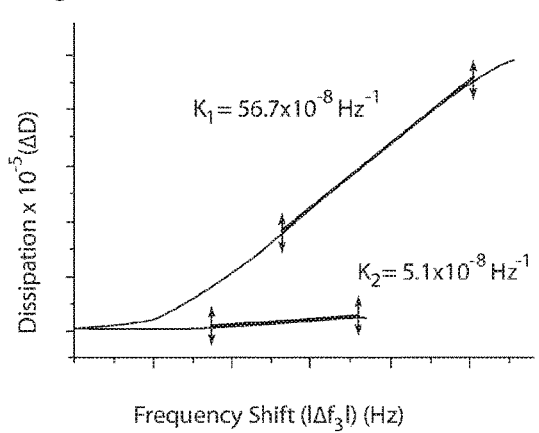

The measurements done at constant peptide concentrations and flow rates of peptide solutions allowed for the continuous monitoring of the SaNet assembly as a linear function of the material mass deposited on the crystal surface. Here plotting changes in dissipation (ΔD) versus resonance frequency changes (Δf) provides an estimate of how new added mass affects the structure on the surface. FIG. 7f shows QCM-D ΔD versus |Δf| plot. K1 and K2 correspond to the plot slopes for D2 and SaNet, respectively.

Figure 6B:
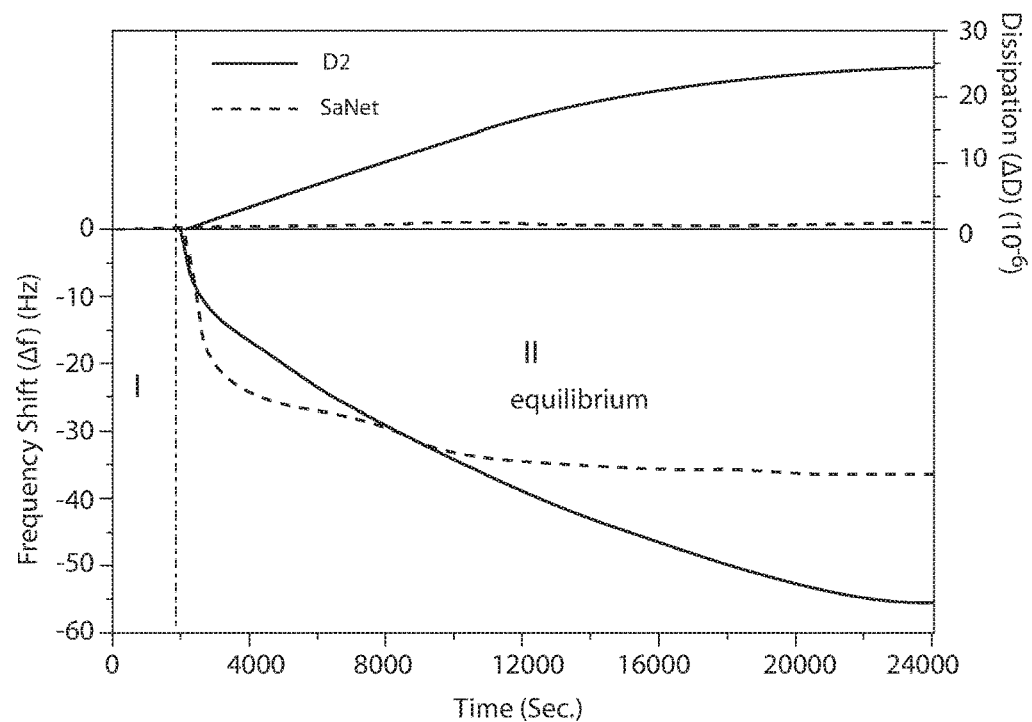

FIG. 6b shows QCM-D responses (both frequency shift and dissipation) for peptide adsorption on silicon dioxide-coated quartz crystals. Discontinuous and continuous lines correspond to SaNet and D2 (see Table 1), respectively. In the upper half of the Figure, changes in dissipation with time due to peptide adsorption are shown and correspond to the right axis. The lower half shows the simultaneous frequency shift of the crystal due to peptide adsorption and relates to the left axis. Regions I and II correspond to the buffer contribution and peptide adsorption, respectively.

The slope of the plot in FIG. 7f is given by K, which is indicative of structure formation and kinetics during adsorption. A small value of K indicates the formation of a structured and rigid layer, which is in contrast to dissipated layer formation characterised by high K values. The returned K2(SaNet) values were an order of magnitude smaller when compared to K1(D2), which is consistent with that SaNet assembled into highly elongated fibrillar structures and with that D2 non-specifically precipitated forming a loosely bonded viscous layer. Further, while D2 precipitated continuously, as expected for a non-equilibrating system, the assembled SaNet reached equilibrium with monomers in solution after the first 3-4 hours, with only additive changes in Δf after (FIGS. 7f and 6b). These results fully support a specific self-assembly process driven by minimised AG and are in good agreement with the folding and assembly data.

Example 3—Differential Cell Adhesion and Proliferation

Human dermal fibroblasts (Invitrogen, UK) were maintained in Medium 106 supplemented with low serum growth supplement (2% v/v) and antibiotics (10 µg/mL gentamicin; 0.25 µg/mL amphotericin B) in 25 cm$^3$ culture flasks. The cells were incubated at 37° C., 5% $CO_2$ and 95% air humidity. At 70-80% confluency cells were washed with PBS to remove the unattached cells and then adhered cells were trypsinised (trypsin/EDTA 0.025:0.01%) followed by trypsin neutraliser (all from Invitrogen, UK). The harvested cells (of passages 3 to 5) were seeded for subsequent cellular analysis.

Cells were seeded at a density of $4 \times 10^3$ in serum-free media for cell viability and proliferation assays on substrates (sterile 96 well plates) coated with 50 µL of peptide (100 µM) or protein (500 µg/mL). For cytoskeletal visualisation Nunc LabTek chambered cover glass slides were used as substrates.

Cell proliferation rates and viability were determined by PrestoBlue®, Vybrant® MTT and CyQUANT® assays on day 1, 4 and 8 (all from Life Technologies, UK).

PrestoBlue® reagent is supplied as a 10× solution and added to each well by diluting (1×) in the serum-free culture medium. The cells were incubated for 30 minutes at 37° C. in 200 µL of the reagent. The fluorescence of each well was measured with a microplate reader (BMG Labtech, Germany), with 544 nm excitation and 590 nm emission filters. Standard calibration curves were generated by plotting measured fluorescence values versus cell numbers. A cell dilution series (500-50000 cells) was done by seeding cells on sterile 96-well plates with overnight incubation before each given time point.

Vybrant® MTT assay: For the colourimetric 3-(4, 5-dimethylthiazole-2-yl)-2, 5-diphenyl tetrazolium bromide (MTT) cell proliferation assay, the cell medium was removed from each well at the set time points and washed with PBS followed by the addition of MTT solution (10 µL, 5 mg/mL in PBS) and serum-free fresh media (100 µL). Following 4-hrs incubations with the reagent at 37° C., the resultant formazan crystals were dissolved in dimethyl sulfoxide (50 µL) according to the manufacture's protocol. The absorbance intensity was measured by a microplate reader at 540 nm with a reference wavelength at 640 nm. Standard calibration curves were generated by plotting measured absorbance values versus cell numbers. A cell dilution series (500-50000 cells) was done by seeding cells on sterile 96-well plates with overnight incubation before each given time point.

CyQUANT® GR dye was prepared in a cell-lysis buffer (according to the manufacturer's protocols) prior to each experiment by diluting this stock solution (400×) into the buffer. After days 1, 4 and 8, the cells grown on the various substrates were washed gently in PBS and stored in a −70° C. freezer. At the same time, to generate calibration data, a cell pellet ($1 \times 10^6$) prepared to provide a cell dilution series was also frozen. Cells grown on the substrates along with the cell pellet were thawed at 37° C. CyQUANT GR dye in the lysis buffer was added (1 mL) to the pellet and the lysate was re-suspended by brief vortexing. A cell dilution series (500-50000 cells) was created with the CyQUANT GR in cell lysis buffer in a final volume of 200 µL. A standard calibration curve was generated by plotting measured fluorescence values versus cell numbers. To quantify cell numbers grown on the substrates, the same volume of the reagent was added to each well. All of the samples were dark-incubated for 10 minutes at room temperature. The fluorescence of each well was measured with the microplate reader, with 485 nm excitation and 520 nm emission filters.

In order to visualise cytoskeletal structures and filopodia, actin staining was performed using Alexa-Fluor 488® conjugated to phalloidin (Life Technologies, UK). Following 1-, 4- and 8-day incubations, cells were rinsed with warm PBS (pH 7.4), fixed in 10% neutral buffered formalin solution (Sigma Aldrich, UK) for 15 min at room temperature, washed with PBS and permeabilised using 0.1% Triton-X 100 in PBS. Cells were then extensively washed in PBS and incubated for 30 min at room temperature with 10 µg/mL phalloidin in PBS. After post-stain washing with PBS, cells were mounted in ProLong Gold with 4',6-diamidino-2-henylindole (DAPI) (Life Technologies, UK) and imaged using an inverted confocal laser scanning microscope (CLSM) (FV-1000, Olympus).

Figure 9A:
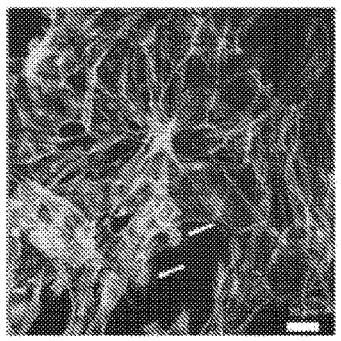
FIG. 9 shows the results of cell growth and proliferation studies.
Figure 9B:
Figure 9C:
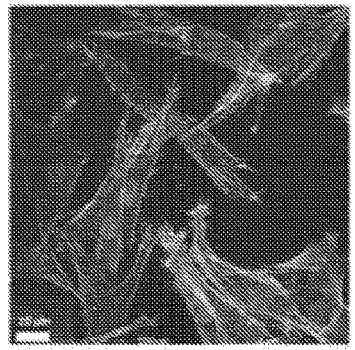
Figure 9D:
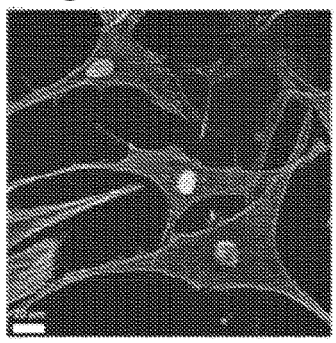
Figure 9E:
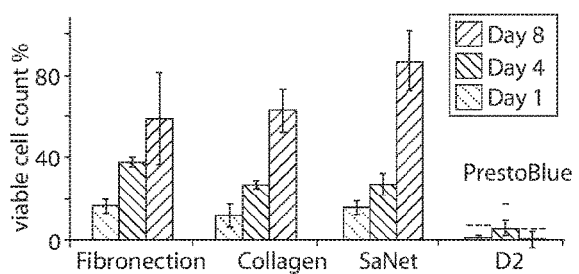
Figure 9F:
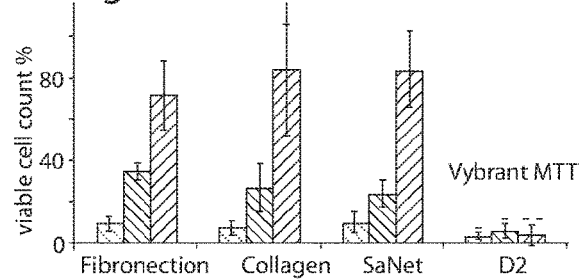
Figure 9G:
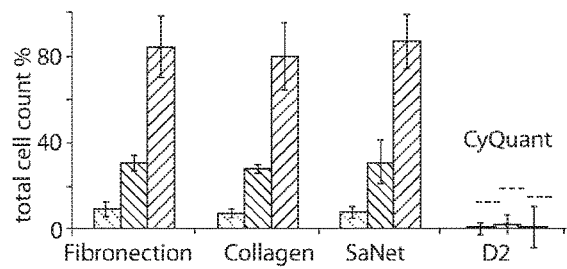

Collectively, the assembly characterisation data confirmed the generation of micrometer-spanning peptide nets as designed. Because their dimensions and relatively homogenous morphology were remarkably similar to those of native matrices the nets were tested as substrates for cell adhesion and proliferation, which were visualised by fluorescence microscopy (FIGS. 9a to 9d) and were monitored and quantified using three different cell proliferation assays (FIGS. 9e to 9g). Human dermal fibroblasts (HDFs) were seeded on five different substrates: bare plastic, taken as a background, substrates coated with SaNet and D2, as a negative non-assembling peptide control, as well as collagen and fibronectin substrates used as positive fibrillar and matrix protein controls, respectively.

FIG. 9 illustrates the results of the cell growth and proliferation studies. Fluorescence micrographs of HDFs incubated on SaNet and fibronectin for a week (FIGS. 9a and 9b) and for 24 hours (FIGS. 9c and 9d) are shown. Fluorescent stains Alexa-Fluor 488® phalloidin and 4',6-diamidino-2-phenylindole highlight actin and nuclear DNA, respectively. In FIG. 9a white arrows point to visible filopodia protrusions. The total viable cell count (FIGS. 9e and 9f) and total cell count FIG. 9g were determined by Presto-Blue® (FIG. 9e), Vybrant® MTT (FIG. 9f) and CyQUANT® (FIG. 9g) assays. The total number of cells on SaNet on day 8 was taken as 100% (SaNet highest for FIGS. 9e and g) after subtracting the background adhesion (bare plastic). According to the analysis of variance (ANOVA) followed by a Fisher post-test for three independent experiments done in triplicate, cells grown on D2 substrates when compared to the other substrates had significantly lower numbers of metabolically active cells on (FIG. 9e) days 1 ($p<0.001$)+, 4 ($p<0.05$) and 8 ($p<0.001$); (FIG. 9f) on days 1 ($p<0.05$), 4 ($p<0.05$) and 8 ($p<0.01$); and (FIG. 9g) significantly lower total numbers of cells on days 1 ($p<0.001$)+, 4 ($p<0.001$) and 8 ($p<0.001$). Significant differences are represented with * for $p<0.05$,  for $p<0.01$ and * for $p<0.001$. (+Other post-tests used (Scheffe, Tukey, Bonholm, Sidakaholm, Bonferroni and Sidak) returned similar values within $p<0.01$-$0.001$ ranges for given pairs of data sets. Incubation conditions: 50 µL of SaNet (100 µM), fibronectin and collagen (500 µg/mL).)

The PrestoBlue® and Vybrant® MTT cell proliferation and viability assays, which are quantitative chemical and enzymatic redox indicators of metabolically active cells, revealed that SaNet-coated substrates strongly promoted cell adhesion and proliferation, with cells remaining viable over a week (FIGS. 9e and 9f).

Similar results were obtained by the CyQUANT® cell assay (FIG. 9g), which does not depend on the metabolic activity of cells or potential factors that can influence its measurement, but provides a direct measure of total cell numbers based on the total nucleic acid content. As seen in FIG. 9, all three tests gave comparable values, expressed as the percentage of total cells (CyQUANT®) and total cells that are viable (PrestoBlue® and Vybrant® MTT), for fibronectin, collagen and SaNet coatings with same cell proliferation trends (days 1, 4 and 8) (FIGS. 9e and 9g). In contrast, all three tests detected only negligible cellular responses for D2 substrates (FIGS. 9e to 9g).

Figure 10:
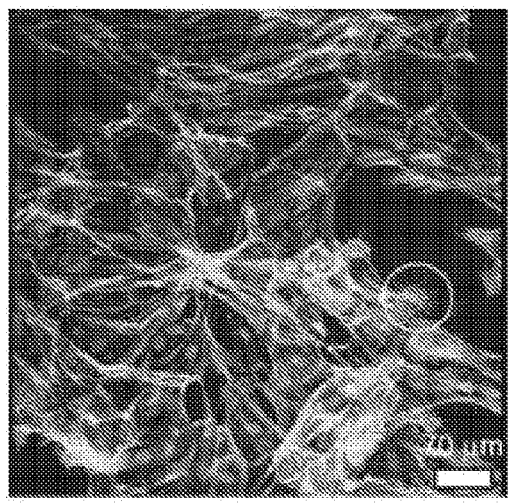
FIG. 10 shows fluorescence micrographs of human dermal fibroblasts.
Figure 10:
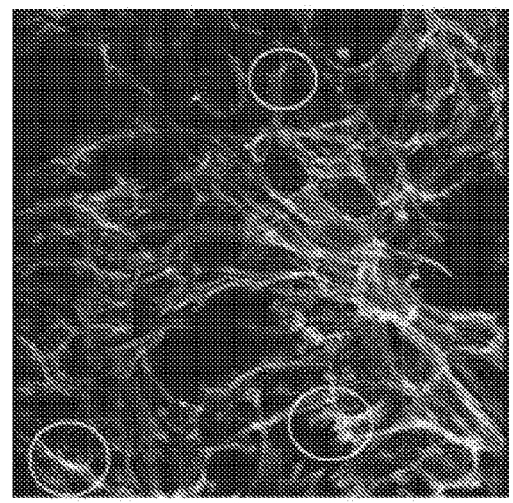
Figure 10:
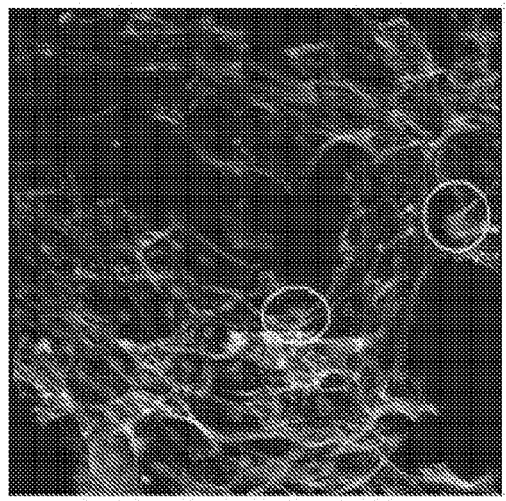

It should be noted here that unlike collagen and fibronectin, SaNet lacks established cell recognition motifs and may not promote cell attachment through chemical cues suggesting that its function should be provided by the specific morphology of the nets. In this light, the most notable differences were observed in cell behaviour for SaNet substrates which revealed brushed filopodia protrusions and, at early stages of cell proliferation, seemingly smaller cells (FIGS. 9a and 9c). However, the effect of reduced cell sizes was not ubiquitous for SaNet samples, unlike filopodia protrusions, which were abundant. The protrusions were reminiscent of actin-supported growth cones and were most apparent at mobile edges of the cells that in turn tended to weave into intricate cellular networks, which might or might not be best accommodated by reducing cell sizes (FIGS. 9a, 9c and 10). FIG. 10 shows fluorescence micrographs showing network-like proliferation patterns of human dermal fibroblasts incubated on SaNet. White circles highlight some filopodia protrusions of individual cells. Given that filopodia are characteristic of transient adhesions of actively migrating cells and help cells probe their substratum and environmental cues, the enhanced filopodia formation suggests enhanced cellular responses to physical features of the SaNet matrix (FIGS. 9a, 9c, 10 and 11a).

Figure 11A:
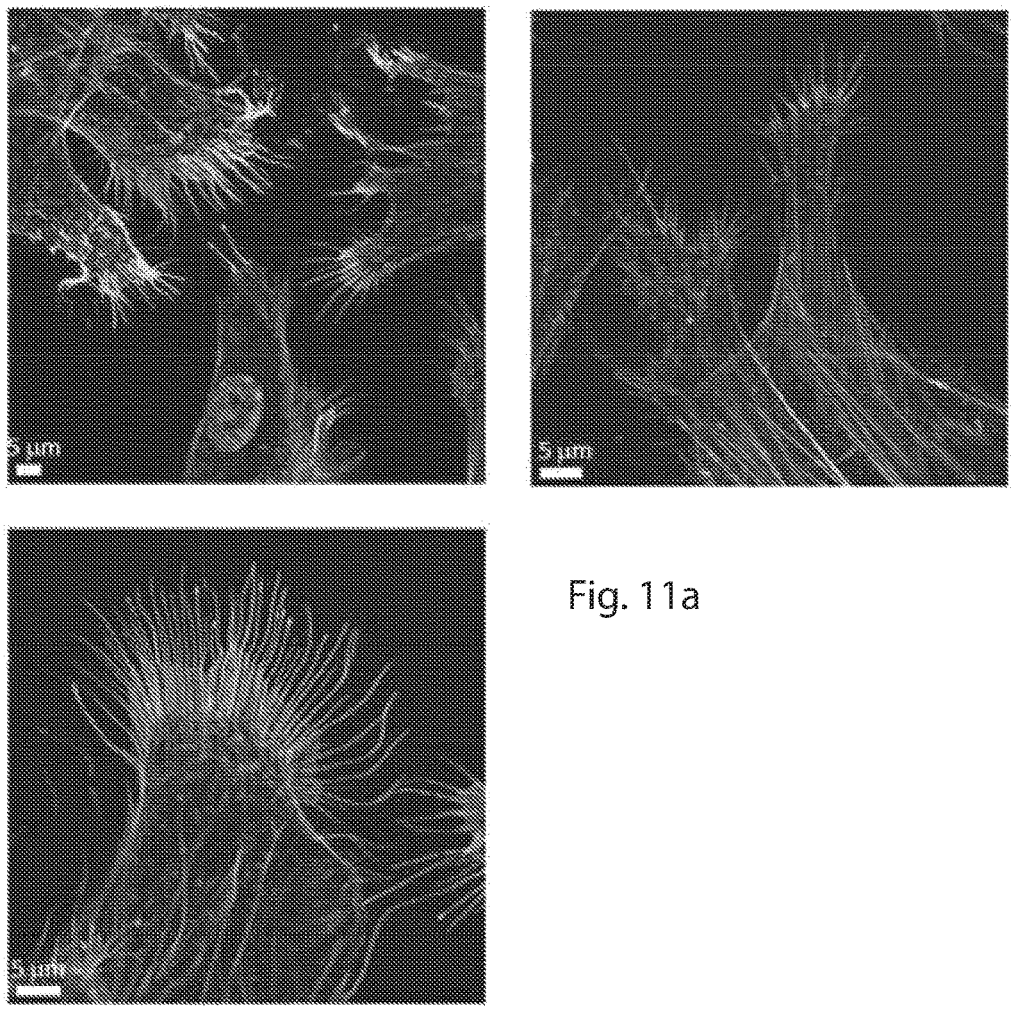
FIG. 11 shows filopodia-rich protrusions in human dermal fibroblasts.
Figure 11B:
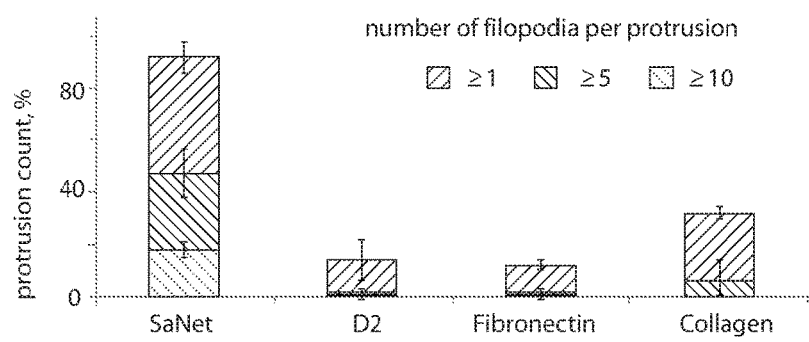

FIG. 11 shows filopodia-rich protrusions on SaNet. FIG. 11a shows fluorescence microscopy images of filopodia protrusions on cells grown for 24 hours. In FIG. 11b total counts of protrusions with filopodia for each substrate are given in percentage derived from the actual number of filopodia-rich protrusions ($\geq 1$, $\geq 5$ or $\geq 10$) divided by the total number of protrusions ($\geq 1$) after subtracting the background number (bare plastic). Protrusions with $\geq 10$ filopodia were observed only for SaNet. According to ANOVA followed by a Fisher post-test for three independent experiments done in triplicate, cells grown on SaNet had significantly ($p<0.001$) higher numbers of filopodia in comparison to any of the other substrates. The counts given in FIG. 11b are averages measured over 10 regions of ×60 confocal micrographs.

None of the other substrates used, and notably fibrous collagen, showed these or similar effects, which, to the best of the applicant's knowledge, have not been reported for any other mimetic system. Therefore, the observed behaviour should be attributed to the physico-morphological properties and the unique architecture of the SaNet matrix. Indeed, whilst the micrometer-spanning nets can sustain cell proliferation and viability (FIG. 9), specific elements of their morphology appear to elicit locally enhanced responses of individual cells (through filopodia formation) and distinctive proliferation patterns (FIGS. 9a and 9c, 10 and 11a).

Comparative impedance measurements using cell-electrode interfaces, which allow evaluating changes in effective impedance (resistance) to applied alternating current, provided further support for different cell proliferation patterns that were measured continuously in real time. Typically, cell attachments to electrode surfaces give impedance increases, whereas changes in cell morphology (cell rounding-up and detachment) cause impedance drops. Resistance traces that can correspond to different events including changes in cellular morphology, patterning and growth rates were recorded as a function of time, with cells seeded in a serum-depleted medium to avoid interferences by serum, which can modulate same signaling pathways for cell adhesion.

Impedance measurements were performed using an xCELLigence system according to the manufacturer's protocols (Roche, UK; ACEA Biosciences, USA). Each electrode array comprises 16 wells, each of which was first coated with assembled SaNet and protein solutions and background measurements were carried out prior to cell seeding. Cells ($10^4$ per well) cultured as described above were seeded on the pre-coated wells. The electrical impedance of each well was automatically recorded every 5 min for the first 24 hours and then every 30 min till the end, and were normalised and expressed using the proprietary software as normalised cell index. Bacterial adhesions were measured every 5 min for over 15 hours.

Figure 12A:
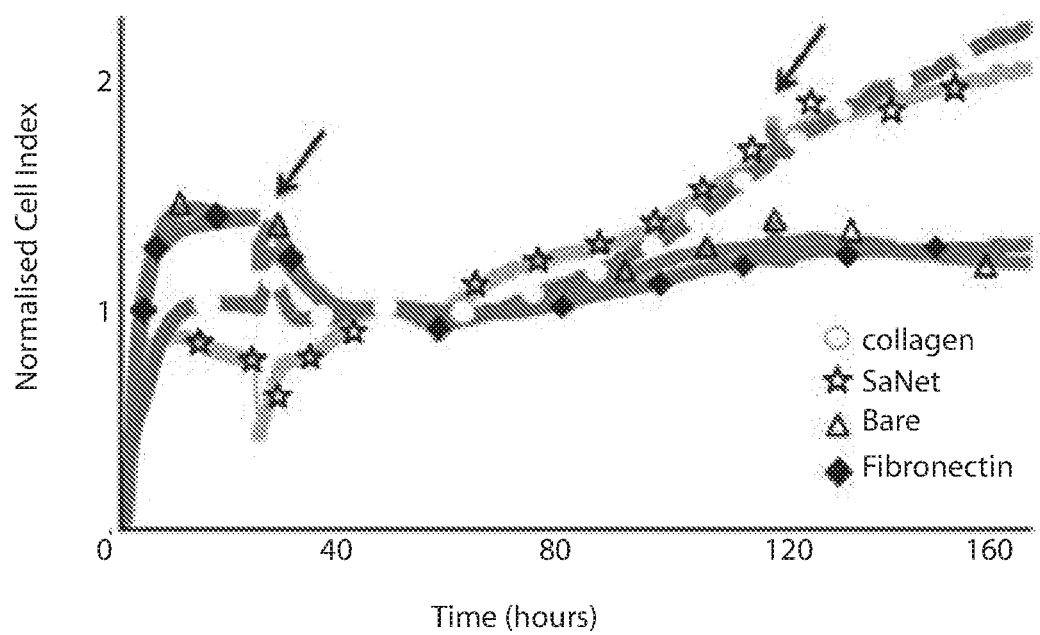
FIG. 12 shows impedance of human dermal fibroblasts and *B. subtilis*.

FIG. 12a shows normalised impedance of HDFs grown on collagen (white spots), SaNet (stars), fibronectin (diamonds) and bare (triangles) substrates. The arrows indicate second and third media inoculations.

Impedance for fibronectin substrates increased sharply compared with that of collagen and SaNet substrates (FIG. 12a), which was likely due to the non-specific sedimentation of HDFs on the electrodes, which was also apparent for bare substrates used as controls. Lower initial impedance values recorded for collagen and SaNet coatings may suggest a delayed or more matrix-directed mechanism of cell adhesion. Indeed, after the first eight hours of initial attachment and spreading, a lag phase showing relatively stabilised patterns for all substrates followed (FIG. 12a). The second medium inoculation was followed by steady decays in resistance curves for fibronectin and bare substrates up to the point of a next cell doubling (40-50 hours), whereupon no substantial changes in impedance were observed. In contrast, a gradually ascending phase in impedance was recorded for fibrillar substrates, SaNet and collagen, suggesting comparable cellular responses (FIG. 12a).

Because SaNet surfaces do not contain known cell recognition motifs such responses cannot result from specific receptor-ligand interactions, as they may do in the case of collagen and fibronectin coatings. Equally importantly, cell responses to SaNet observed in all tests cannot be mediated by the SaNet binding to cellular membranes.

Solution-phase flow LD spectra were recorded on a Jasco-810 spectropolarimetre using a photo-elastic modulator ½ wave plate, and a micro-volume quartz cuvette flow cell with ~0.25 mm annular gap and quartz capillaries (all from Kromatec Ltd, UK). Molecular alignment was achieved through the constant flow of the sample solution between two coaxial cylinders—a stationary quartz rod and a rotating cylindrical capillary. LD spectra were acquired with laminar flow obtained by maintaining the rotation speed at 3000 rpm and processed by subtracting non-rotating baseline spectra. LD spectra recorded in the presence of synthetic membranes were prepared at a lipid:peptide molar ratio of 100:1 (3 mM total lipid, 30 µM peptide).

Linear dichroism (LD) spectroscopy, which gives a straightforward probe of relative orientation of peptide binding in membranes revealed that SaNet did not specifically orient on mammalian mimetic membranes (zwitterionic unilamellar vesicles), suggesting that no interactions occurred. In marked contrast, LD spectra recorded in the presence of bacterial mimetic membranes (anionic unilamellar vesicles) were characteristic of the on-surface orientation of SaNet helices with typical minima at 195-200 nm and 222-225 nm and a maximum at 205-210 nm. Lipid vesicles were used as bacterial membrane mimetics and were prepared as follows: The lipids, 1,2-dilauroylphosphatidylcholine (DLPC) and 1,2-dilauroyl-sn-glycero-3-phospho-(1'-rac-glycerol) (DLPG), 75%/25% (w/w) used for liposome construction were from Avanti Polar Lipids. The lipids were weighted up, dissolved in chloroform-methanol (2:1, v/v), dried under a nitrogen stream, and placed under vacuum overnight. The resulting film was hydrated to 10 mg/mL total lipid concentration in 10 mM phosphate buffer, pH 7.4. The suspension was then extensively vortexed, sonicated (30° C.) and extruded (fifteen times) through polycarbonate filters (0.05 µm) using a hand-held extruder (Avanti Polar Lipids) to give a clear solution containing small unilamellar vesicles (SUV), which were analysed (50 nm) by photon correlation spectroscopy (as described above) following the re-suspension of vesicles to a final concentration of 1 mg/m L.

Figure 13A:
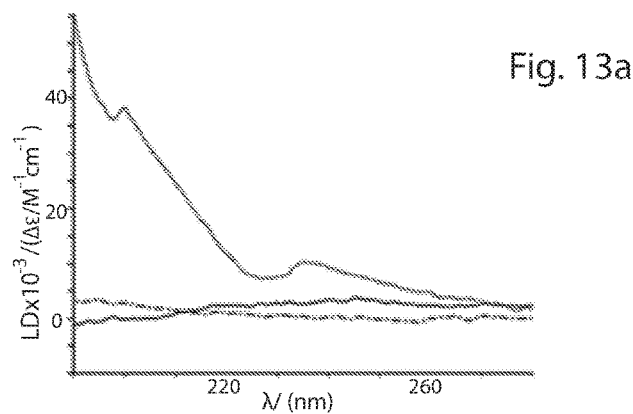
FIG. 13 shows membrane and bacterial cell interactions and *E. coli* colonisation fluorescent micrographs.

FIG. 13a, shows LD spectra for assembled SaNet in 10 mM phosphate buffer (solid line) and in the presence of mammalian (dash-dotted line) and microbial (dotted line) mimetic membranes. (Folding conditions: lipid-peptide ratio 100:1 (30 µM peptide), 20° C. in 10 mM phosphate buffer, pH 7.4.)

These LD spectra indicate that SaNet, through predominantly cationic domains, interacts with the anionic membranes and aligns parallel to their surfaces. This is important for two reasons.

Firstly, it implies that SaNet can elicit differential membrane responses discriminating the proliferation of one cell class from another. Cell proliferation supports multicellular living and is essential for tissue organisation. However, it is not limited to eukaryotes. A prominent example is bacterial biofilm formation—a multicellular phenomenon implicated in a variety of infectious events that compromise normal tissue development and healing. Biofilms rapidly mature from initial bacterial adhesion on surfaces, which unless rendered antimicrobial remain attractive substrates for persistent bacterial colonisation. Existing attempts to deter biofilm formation include physical and chemical surface modifications and the use of polymeric hydrogels, but these are specialist antimicrobial strategies that are not necessarily supportive of primary cell proliferation and may not be readily tailored for it.

Secondly, which is directly relevant to the first point, SaNet design is intrinsically, albeit moderately, antimicrobial. The split 2+1 pattern of the SaNet block provides cationic two-heptad stretches, D2, that exhibit weakly antimicrobial activities, which become amplified and apparent in the matrix (see FIG. 3d). This should make the matrix responsive to local bacterial adhesion, and more to individual cells rather than to the bulk bacterial culture. Individual D2 domains are too short to span or porate membranes, but may be able to resist biofilm formation as a coating on the surface. However, it is in the assembled matrix, in which they are pre-folded to cover every third nanometer and at least 50% of its solvent exposed area, where the activity becomes most pronounced. A small fraction of a higher order fibre (see FIG. 4c) is equal to the size of a bacterial cell (<2 µm), which upon adhering to the matrix can compete for cationic D2 domains. The affinity of these localised cationic domains to bacterial membranes is competitively higher than that for their complementary anionic domains, which is supported by LD experiments showing that SaNet responds only to the bacterial membrane mimetics adopting a specific orientation, which in turn can be achieved only through strong binding. The continuous arrangement of the domains can thus be viewed as an antimicrobial "carpet" that is sufficient to furnish bacteria-repellent surfaces.

Bacterial inocula (E. coli and B. subtilis) were prepared in Mueller Hinton broth at A600 of 0.6, then diluted to 1:100 in the pre-warmed medium, and 50 µL of this dilution was added to each well of the coated Nunc LabTek chambered cover glass slides. Formed biofilms were analysed after 16-hour incubations using a Live/Dead BacLight bacterial viability stain kit (Molecular Probes, UK), and were visualised by a confocal laser scanning microscope (CLSM) (FV-1000, Olympus). Bacterial viability was quantitatively probed by using PrestoBlue® reagent, as used for the cell viability and proliferation assay. E. coli was seeded at the same density as above in sterile bare and coated 96-well plates. After 16 hours incubation at 37° C. (or 30° C. for B. subtilis), the biofilm formed on each substrate was carefully washed with 10 mM Tris-HCl buffer, pH 7, to remove bacteria remaining in suspension. Two hundred microliters of PrestoBlue® reagent diluted in Mueller Hinton broth were added to each well and incubated for 30 minutes at 37° C. The fluorescence of each well was measured using a microplate reader with 544 nm excitation and 590 nm emission filters.

Figure 13B:
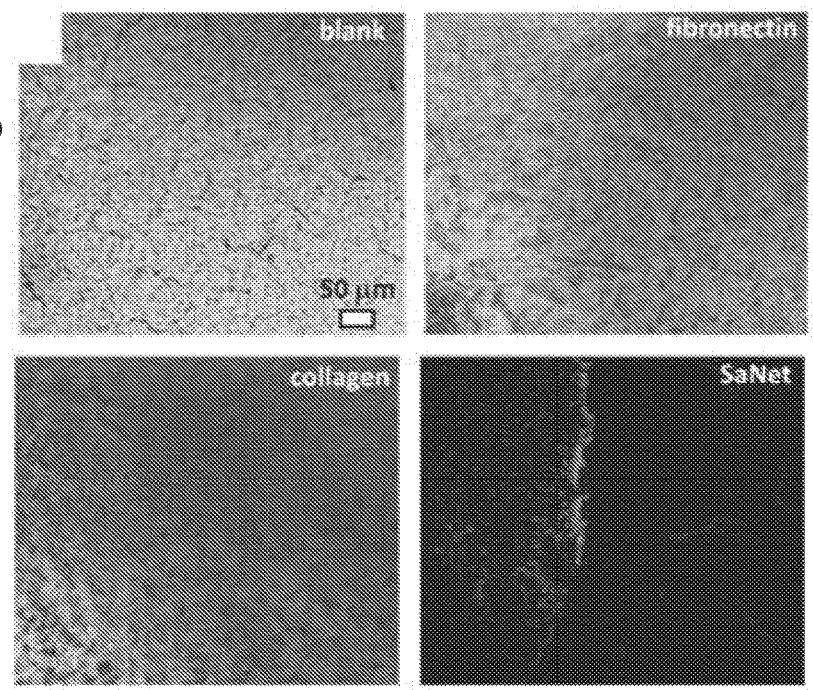
Figure 13C:
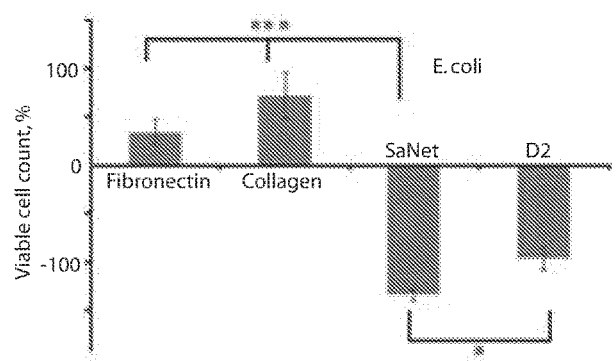

FIG. 13b and FIG. 13c are fluorescence micrographs and total viable cell counts respectively determined by PrestoBlue® of E. coli after 16-hour incubations on different substrates. Total viable cell counts are given in percentage after subtracting the background adhesion (bare plastic), which was taken as 100%. The viability of cells grown on SaNet is significantly lower in comparison to fibronectin and collagen (p<0.001) and to D2 (p<0.01) according to ANOVA followed by a Fisher post-test for three independent experiments done in triplicate.

Figure 14:
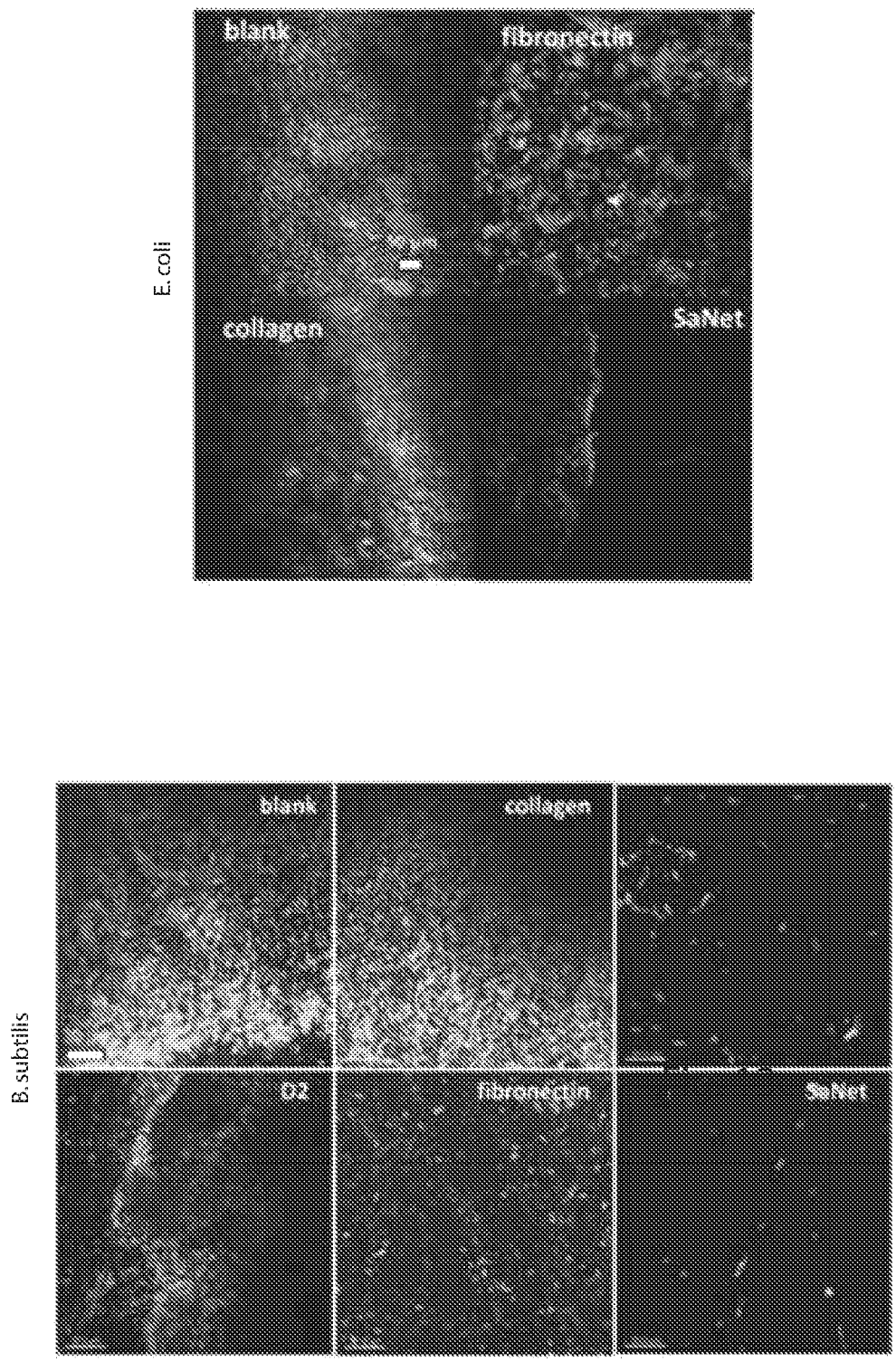
FIG. 14 shows *E. coli* and *B. subtilis* colonisation studies.

As can be seen, SaNet substrates were found to be strongly resistant against bacterial adhesion over 16-hour incubations and showed quantitatively stronger responses when compared with D2 control (FIGS. 13b, 13c and FIG. 14, which shows fluorescence micrographs of E. coli and B. subtilis cells seeded on different substrates).

Figure 12B:
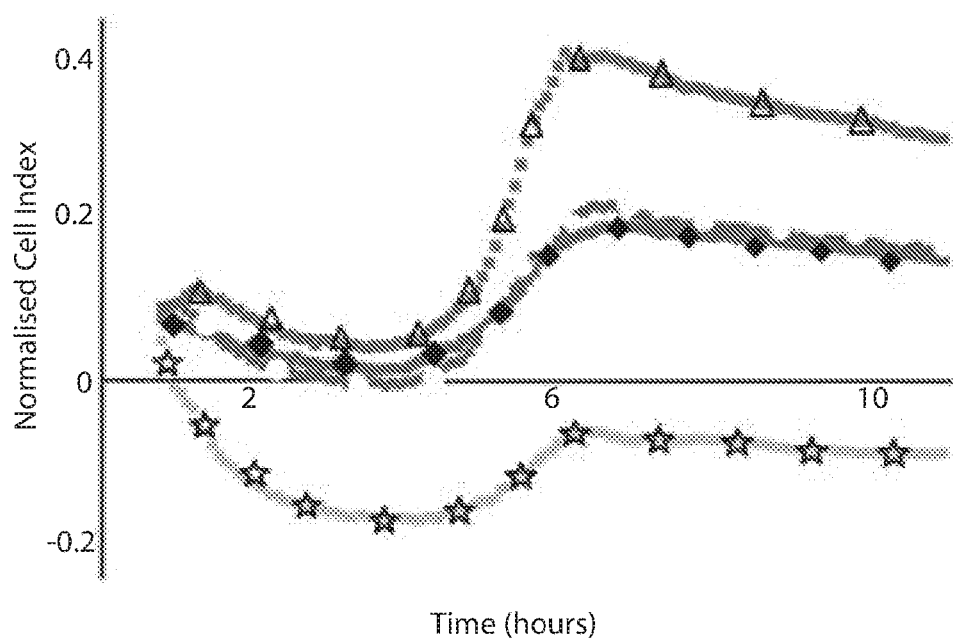

FIG. 12b shows normalised impedance of B. subtilis grown on collagen (white spots), SaNet (stars), fibronectin (diamonds) and bare (triangles) substrates. The arrows indicate second and third media inoculations.

Impedance for SaNet remained in a negative phase with no signs of positive recovery over 15 hours (FIG. 12b). In contrast, the natural substrates used in the study (fibronectin and collagen), which do not have antimicrobial properties, did not resist biofilm formation (FIGS. 12b, 13b, 13c, and 14).

Minimum inhibitory concentrations (MIC) were determined by broth microdilution on P. aeruginosa ATCC 27853, E. coli K12, S. aureus ATCC 25723, M. luteus NCIMB 13267 and B. subtilis ATCC 6633 according to the Clinical and Laboratory Standards Institute. Typically, 100 µl of 0.5-1×106 CFU per ml of each bacterium in Mueller Hinton broth was incubated in 96 well plates with 100 mL of serial two-fold dilutions of the peptides (final concentrations, 100-0 mM) at 37° C. (or 30° C. for B. subtilis and M. luteus) on a 3D orbital shaker. The absorbance was measured after peptide addition at 600 nm using a Victor 2 plate reader (Perkin Elmer). Minimum inhibitory concentrations (MICs) were defined as the lowest peptide concentration showing growth inhibition after 24 hours at 37° C. All tests were done in triplicate.

Haemolysis was determined by incubating 10% (v/v) suspension of human erythrocytes with peptides. Erythrocytes were rinsed 4 times in 10 mM PBS, pH 7.2, by repeated centrifugation and re-suspension (3 min, 3000×g). Erythrocytes were incubated at room temperature for 1 hour in either deionised water (fully haemolysed control), PBS or with peptide in PBS. After centrifugation at 10 000 g for 5 min, the supernatant was separated from the pellet and the absorbance measured at 550 nm. Absorbance of the suspension treated with deionised water defined complete haemolysis. The values given in Table 2 correspond to concentrations needed to kill a half of the sample population (50% lysis of human erythrocytes) and are expressed as median lethal concentrations—LC50. All tests were done in triplicate.

Moderate antimicrobial and negligible haemolytic activities for SaNet peptide measured using the microdilution assay (see Table 2 below) provided complementary evidence that it is the assembled SaNet that deters bacterial colonisation and promotes mammalian cell proliferation.

TABLE 2

Biological activity of SaNet

| Bacterium | MIC, µM |
|---|---|
| E. coli (K12) | 100 |
| P. aeruginosa (ATCC 27853) | >100 |
| S. aureus (ATCC 6538) | >100 |
| B. subtilis (ATCC 6633) | 50 |
| M. luteus | <50 |
| | $LC_{50}$, µM |
| Human erythrocytes | >>600 |

Figure 15:
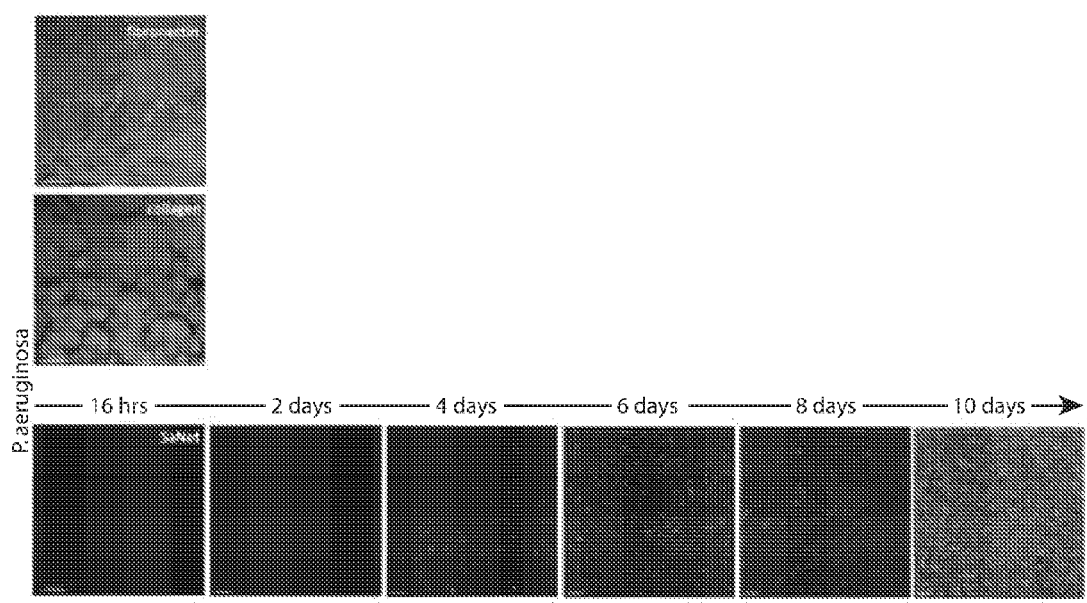
FIG. 15 shows a *P. aeruginosa* colonisation study.

FIG. 15 shows the results of a P. aeruginosa colonisation study. P. aeruginosa cells were incubated on SaNet substrates over 10 days, and fluorescence micrographs were taken at different time points. Corresponding micrographs for bacteria incubated over 16 hours on collagen and fibronectin substrates were used as controls and are shown for comparison. It can be seen that the SaNet substrate inhibits bacterial growth for at least two days.

Given that the time period of several days to a week, employed in this study, is deemed sufficient for mammalian cells to produce their own matrix and that biofilm deterrence is most critical during the first days of tissue restoration, the demonstrated differential impact of the matrix on cell adhesion and proliferation holds particular promise for biomedical applications as a biodegradable cell-supporting and tissue-protecting scaffold or coating.

Statistical Analysis:

Statistical analysis for all the analytical data was performed by OriginPro 8.5 using ANOVA followed by a Fisher post-test for three independent experiments done in triplicate. Other multiple-means comparisons tests (Bonferroni, Tukey, Sidak, Bonholm, Scheffe and Sidakholm), with p values <0.05 considered significant, were also performed to allow comparison. The results are expressed as an average±standard deviation.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in United Kingdom patent application numbers 1320209.8 and 1322749.1, from which the present application claims priority, and in the abstract accompanying this application are incorporated herein by reference.

The invention claimed is:

1. A cyclic peptide including a first domain and a second domain, the first domain and the second domain connected to one another at each end by a linker, wherein each domain includes a plurality of charged sub-domains and includes at least one cationic sub-domain and at least one anionic sub-domain;
   wherein an anionic sub-domain is located at the amino-end of the first domain and at the carboxyl-end of the second domain, and wherein the cationic sub-domain is located at the carboxyl-end of the first domain and the amino-end of the second domain; or
   wherein the first domain comprises the sequence: EIAALEQEIAALEYKIAALK (SEQ ID NO.3) and/or the second domain comprises the sequence: KIAALKQKIAALKQEIAALE (SEQ ID NO.4).

2. A cyclic peptide as claimed in claim 1, wherein within each of the first domain and the second domain there is not an equal number of cationic sub-domains and anionic sub-domains.

3. A cyclic peptide as claimed in claim 1, wherein the first domain and the second domain include an odd number of sub-domains.

4. A cyclic peptide as claimed in 1, wherein the first domain and the second domain do not have the same number of cationic sub-domains as one another, and wherein the first domain and the second domain do not have the same number of anionic sub-domains as one another.

5. A cyclic peptide as claimed in claim 1, wherein the peptide has the formula:

$$((gabcdef)_m(gabcde)_n\text{-}(X)_q(gabcdef)_m(gabcde)_n\text{-}(X)_q)$$

where gabcdef is a heptad repeat motif, X is a flexible linker;
$m \geq 2$; $n \geq 1$; and $q=1$.

6. A cyclic peptide as claimed in claim 1, having the sequence:
   EIAALEQEIAALEYKIAALKGGGKIAALKQKI-AALKQEIAALEGGG (SEQ ID NO.5).

7. A synthetic protein network formed from a cyclic peptide as claimed in claim 1.

8. A synthetic protein network as claimed in claim 7, wherein the network is a synthetic extracellular matrix.

9. A synthetic protein network as claimed in claim 7, including eukaryotic cells grown thereon.

10. A synthetic protein network as claimed in claim 9, wherein the eukaryotic cells are vertebrate cells.

11. A method of making a synthetic protein network, including providing a cyclic peptide as claimed claim 1, and allowing the cyclic peptide to self-assemble into the synthetic protein network.

12. A synthetic protein network as claimed in claim 7, wherein the network prevents bacterial adsorption, colonisation and biofilm formation.

* * * * *

SEQUENCE LISTING

<160> NUMBER OF SEQ ID NOS: 11

<210> SEQ ID NO 1
<211> LENGTH: 6
<212> TYPE: PRT
<213> ORGANISM: Artificial Sequence
<220> FEATURE:
<223> OTHER INFORMATION: Anionic sub-domain

<400> SEQUENCE: 1

Glu Ile Ala Ala Leu Glu

```
<210> SEQ ID NO 2
<211> LENGTH: 6
<212> TYPE: PRT
<213> ORGANISM: Artificial Sequence
<220> FEATURE:
<223> OTHER INFORMATION: Cationic sub-domain

<400> SEQUENCE: 2

Lys Ile Ala Ala Leu Lys
1               5

<210> SEQ ID NO 3
<211> LENGTH: 20
<212> TYPE: PRT
<213> ORGANISM: Artificial Sequence
<220> FEATURE:
<223> OTHER INFORMATION: First domain

<400> SEQUENCE: 3

Glu Ile Ala Ala Leu Glu Gln Glu Ile Ala Ala Leu Glu Tyr Lys Ile
1               5                   10                  15

Ala Ala Leu Lys
            20

<210> SEQ ID NO 4
<211> LENGTH: 20
<212> TYPE: PRT
<213> ORGANISM: Artificial Sequence
<220> FEATURE:
<223> OTHER INFORMATION: Second domain

<400> SEQUENCE: 4

Lys Ile Ala Ala Leu Lys Gln Lys Ile Ala Ala Leu Lys Gln Glu Ile
1               5                   10                  15

Ala Ala Leu Glu
            20

<210> SEQ ID NO 5
<211> LENGTH: 46
<212> TYPE: PRT
<213> ORGANISM: Artificial Sequence
<220> FEATURE:
<223> OTHER INFORMATION: Cyclic peptide

<400> SEQUENCE: 5

Glu Ile Ala Ala Leu Glu Gln Glu Ile Ala Ala Leu Glu Tyr Lys Ile
1               5                   10                  15

Ala Ala Leu Lys Gly Gly Gly Lys Ile Ala Ala Leu Lys Gln Lys Ile
            20                  25                  30

Ala Ala Leu Lys Gln Glu Ile Ala Ala Leu Glu Gly Gly Gly
            35                  40                  45

<210> SEQ ID NO 6
<211> LENGTH: 7
<212> TYPE: PRT
<213> ORGANISM: Artificial Sequence
<220> FEATURE:
<223> OTHER INFORMATION: Anionic sub-domain

<400> SEQUENCE: 6

Glu Ile Ala Ala Leu Glu Gln
1               5
```

<210> SEQ ID NO 7
<211> LENGTH: 7
<212> TYPE: PRT
<213> ORGANISM: Artificial Sequence
<220> FEATURE:
<223> OTHER INFORMATION: Anionic sub-domain

<400> SEQUENCE: 7

Glu Ile Ala Ala Leu Glu Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: Cationic sub-domain

<400> SEQUENCE: 8

Lys Ile Ala Ala Leu Lys Gln
1               5

<210> SEQ ID NO 9
<211> LENGTH: 20
<212> TYPE: PRT
<213> ORGANISM: Artificial Sequence
<220> FEATURE:
<223> OTHER INFORMATION: Second domain

<400> SEQUENCE: 9

Lys Ile Ala Ala Leu Lys Gln Lys Ile Ala Ala Leu Lys Tyr Glu Ile
1               5                   10                  15

Ala Ala Leu Glu
            20

<210> SEQ ID NO 10
<211> LENGTH: 45
<212> TYPE: PRT
<213> ORGANISM: Artificial Sequence
<220> FEATURE:
<223> OTHER INFORMATION: Partial cyclic peptide

<400> SEQUENCE: 10

Glu Ile Ala Ala Leu Glu Gly Gly Gly Glu Ile Ala Ala Leu Glu Gln
1               5                   10                  15

Glu Ile Ala Ala Leu Glu Tyr Lys Ile Ala Ala Leu Lys Gly Gly Gly
            20                  25                  30

Lys Ile Ala Ala Leu Lys Gln Lys Ile Ala Ala Leu Lys
        35                  40                  45

<210> SEQ ID NO 11
<211> LENGTH: 14
<212> TYPE: PRT
<213> ORGANISM: Artificial sequence
<220> FEATURE:
<223> OTHER INFORMATION: synthetic polypeptide

<400> SEQUENCE: 11

Lys Ile Ala Ala Leu Lys Gln Lys Ile Ala Ala Leu Lys Gln
1               5                   10